US011102962B2

(12) United States Patent
Wang et al.

(10) Patent No.: US 11,102,962 B2
(45) Date of Patent: *Aug. 31, 2021

(54) HUMANIZED IL-6 AND IL-6 RECEPTOR

(71) Applicant: Regeneron Pharmaceuticals, Inc., Tarrytown, NY (US)

(72) Inventors: Li-Hsien Wang, Somers, NY (US); Anthony T. Dore, Jr., Tarrytown, NY (US); Sean Stevens, Del Mar, CA (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/502,197

(22) Filed: Jul. 3, 2019

(65) Prior Publication Data
US 2020/0008407 A1 Jan. 9, 2020

Related U.S. Application Data

(60) Continuation of application No. 16/001,074, filed on Jun. 6, 2018, now Pat. No. 10,433,528, which is a continuation of application No. 15/350,739, filed on Nov. 14, 2016, now Pat. No. 10,004,211, which is a continuation of application No. 15/177,582, filed on Jun. 9, 2016, now Pat. No. 9,622,460, which is a division of application No. 14/735,710, filed on Jun. 10, 2015, now Pat. No. 9,392,777, which is a continuation of application No. 14/490,877, filed on Sep. 19, 2014, now Pat. No. 9,078,418, which is a continuation of application No. 13/662,880, filed on Oct. 29, 2012, now Pat. No. 8,878,001.

(60) Provisional application No. 61/556,579, filed on Nov. 7, 2011, provisional application No. 61/552,900, filed on Oct. 28, 2011.

(51) Int. Cl.
| | |
|---|---|
| A01K 67/027 | (2006.01) |
| C12N 15/00 | (2006.01) |
| C12N 5/07 | (2010.01) |
| C12N 5/10 | (2006.01) |
| C07K 14/54 | (2006.01) |
| C07K 14/715 | (2006.01) |
| C12N 5/0735 | (2010.01) |
| C12N 5/16 | (2006.01) |
| C12N 15/90 | (2006.01) |

(52) U.S. Cl.
CPC ...... *A01K 67/0278* (2013.01); *C07K 14/5412* (2013.01); *C07K 14/7155* (2013.01); *C12N 5/0606* (2013.01); *C12N 5/10* (2013.01); *C12N 5/16* (2013.01); *C12N 15/907* (2013.01); *A01K 2207/15* (2013.01); *A01K 2217/052* (2013.01); *A01K 2217/072* (2013.01); *A01K 2217/15* (2013.01); *A01K 2227/10* (2013.01); *A01K 2227/105* (2013.01); *A01K 2267/02* (2013.01); *A01K 2267/03* (2013.01); *C07K 2319/00* (2013.01)

(58) Field of Classification Search
CPC ........ A01K 67/0278; C12N 5/07; C12N 5/10; C12N 5/063
USPC ..................... 800/18, 25; 435/352
See application file for complete search history.

(56) References Cited

U.S. PATENT DOCUMENTS

| | | | |
|---|---|---|---|
| 6,100,445 | A | 8/2000 | Seshadri et al. |
| 7,582,298 | B2 | 9/2009 | Stevens et al. |
| 7,759,541 | B2 | 7/2010 | Wolf et al. |
| 8,878,001 | B2 | 11/2014 | Wang et al. |
| 9,078,418 | B2 | 7/2015 | Wang et al. |
| 9,392,777 | B2 | 7/2016 | Wang et al. |
| 9,622,460 | B2 | 4/2017 | Wang et al. |
| 10,004,211 | B2 | 6/2018 | Wang et al. |
| 2011/0200982 | A1 | 8/2011 | Stevens et al. |
| 2013/0042330 | A1 | 2/2013 | Murphy et al. |
| 2013/0111616 | A1 | 5/2013 | MacDonald et al. |
| 2013/0111617 | A1 | 5/2013 | MacDonald et al. |
| 2015/0272092 | A1 | 10/2015 | Wang et al. |
| 2017/0055506 | A1 | 3/2017 | Wang et al. |
| 2018/0271071 | A1 | 9/2018 | Wang et al. |

FOREIGN PATENT DOCUMENTS

| | | |
|---|---|---|
| CA | 2752200 A1 | 7/2014 |
| CN | 101506235 A | 8/2009 |
| EP | 0 791 359 A1 | 8/1997 |
| WO | 2011/044050 A2 | 4/2011 |
| WO | 2011/084664 A1 | 7/2011 |

(Continued)

OTHER PUBLICATIONS

Cho A. et al., "Generation of Transgenic Mice", Curr Protoc Cell Biol., Unit-19.11 (Mar. 2009).

(Continued)

*Primary Examiner* — Valarie E Bertoglio
(74) *Attorney, Agent, or Firm* — Scully, Scott, Murphy & Presser, P.C.; Elysa Goldberg

(57) ABSTRACT

Mice that comprise a replacement of endogenous mouse IL-6 and/or IL-6 receptor genes are described, and methods for making and using the mice. Mice comprising a replacement at an endogenous IL-6Rα locus of mouse ectodomain-encoding sequence with human ectodomain-encoding sequence is provided. Mice comprising a human IL-6 gene under control of mouse IL-6 regulatory elements is also provided, including mice that have a replacement of mouse IL-6-encoding sequence with human IL-6-encoding sequence at an endogenous mouse IL-6 locus.

11 Claims, 15 Drawing Sheets

Specification includes a Sequence Listing.

(56) References Cited

FOREIGN PATENT DOCUMENTS

| WO | 2012/112544 A2 | 8/2012 |
|---|---|---|
| WO | 2013/047729 A1 | 4/2013 |

OTHER PUBLICATIONS

Dicosmo B.F. et al., "Airway Epithelial Cell Expression of Interleukin-6 in Transgenic Mice", The Journal of Clinical Investigation 94:2028-2035 (1994).
Von Felbert V. et al., "Interleukin-6 Gene Ablation in a Transgenic Mouse Model of Malignant Skin Melanoma", American Journal of Pathology 166(3):831-841 (Mar. 2005).
Wilmott R.W. et al., "Generation of a Transgenic Mouse With Lung-Specific Overexpression of the Human Interleukin-1 Receptor Antagonist Protein", Am. J. Respir. Cell Mol. Biol. 18:429-434 (1998).
Indian Examination Report dated Jul. 23, 2019 received in Indian Application No. 3920/CHENP/2014, together with an English-language translation.
Zilberstein A. et al., "Structure and Expression of cDNA and Genes for Human Interferon-Beta-2, a Distinct Species Inducible by Growth-Stimulatory Cytokines", The EMBO Journal 5(10):2529-2537 (1986).
Novus Biologicals-a Bio-Techne Brand, "Human IL-6 Protein 5 Ug", NBP2-34901 (3 pages) (2016).
Written Opinion for PCT/US2012/062379 (7 pages), dated May 3, 2013.
Written Opinion for PCT/US2013/045788 (9 pages), dated Jul. 10, 2013.
International Search Report for PCT/US2012/062379 (5 pages), dated May 3, 2013.
Japanese Notice of Reasons for Rejection dated Aug. 31, 2016 received in Japanese Application No. 2014-539105, together with an English-language translation.
Russian Office Action dated Apr. 21, 2017 received in Russian Application No. 2014121324, together with an English-language translation.
Chinese Notice of Reexamination dated May 4, 2018 received in Chinese Patent Application No. 201280065013.6, together with an English-language translation.
English-language translation of Singapore Search Report and Written Opinion dated Mar. 15, 2019 received in Singapore Application No. 10201600965Y.
Anderson P., "Post-Transcriptional Control of Cytokine Production", Nature Immunology 9(4):353-359 (Apr. 2008).
Appenheimer M.M. et al., "Conservation of IL-6 Trans-Signaling Mechanisms Controlling L-Selectin Adhesion by Fever-Range Thermal Stress", European Journal of Immunology 37:2856-2867 (2007).
Campbell I.L. et al., "Neurologic Disease Induced in Transgenic Mice by Cerebral Overexpression of Interleukin 6", Proc. Natl. Acad. Sci. USA 90:10061-10065 (Nov. 1993).
Clark J. et al., "A Future for Transgenic Livestock", Nature Reviews—Genetics 4:825-833 (Oct. 2003).
De Benedetti F. et al., "Interleukin 6 Causes Growth Impairment in Transgenic Mice Through a Decrease in Insulin-Like Growth Factor-I", J. Clin. Invest. 99(4):643-650 (Feb. 15, 1997).
Dennis JR. M.B., "Welfare Issues of Genetically Modified Animals", ILAR Journal 43(2):100-109 (2002).
Dimitris A. et al., "The Pathophysiologic Roles of Interleukin-6 in Human Disease", Ann Intern Med. 128:127-137 (1998).
Erta M. et al., "Interleukin-6, a Major Cytokine in the Central Nervous System", International Journal of Biological Sciences 8(9):1254-1266 (2012).
Fattori E. et al., "IL-6 Expression in Neurons of Transgenic Mice Causes Reactive Astrocytosis and Increase in Ramified Microglial Cells But No Neuronal Damage", European Journal of Neuroscience 7:2441-2449 (1995).
Fattori E. et al., "Development of Progressive Kidney Damage and Myeloma Kidney in Interleukin-6 Transgenic Mice", Blood 83(9):2570-2579 (May 1, 1994).
Goya S. et al, "Sustained Interleukin-6 Signalling Leads to the Development of Lymphoid Organ-Like Structures in the Lung", Journal of Pathology 200:82-87 (2003).
Heinrich P.C. et al., "Interleukin-6 and the Acute Phase Response", Biochem. J. 265:621-636 (1990).
Hirano T. et al., "Biological and Clinical Aspects of Interleukin 6", Immunology Today 11(12):443-449 (1990).
Hirano T. et al, "Complementary DNA for a Novel Human Interleukin (BSF-2) that Induces B Lymphocytes to Produce Immunoglobulin", Nature 324:73-76 (Nov. 6, 1986).
Hirano T. et al., "Purification to Homogeneity and Characterization of Human B-Cell Differentiation Factor (BCDF or BSFp-2)", Proc. Natl. Acad. Sci. USA 82:5490-5494 (Aug. 1985).
Hirota H. et al, "Continuous Activation of gp130, a Signal-Transducing Receptor Component for Interleukin 6-Related Cytokines, Causes Myocardial Hypertrophy in Mice", Proc. Natl. Acad. Sci. USA 92:4862-4866 (May 1995).
Jacob H.J. et al., "Gene Targeting in the Rat: Advances and Opportunities", Trends in Genetics 26(12):510-518 (Dec. 2010).
Kalueff A.V. et al., "Intranasal Administration of Human IL-6 Increases the Severity of Chemically Induced Seizures in Rats", Neuroscience Letters 365:106-110 (2004).
Keller E.T. et al., "Molecular and Cellular Biology of Interleukin-6 and its Receptor", Frontiers in Bioscience 1:340-357 (1996).
Kishimoto T., "IL-6: From Its Discovery to Clinical Applications", International Immunology 22(5):347-352 (2010).
Kishimoto T., "The Biology of Interleukin-6", Blood 74(1):1-10 (Jul. 1989).
Kovalchuk A.L. et al., "IL-6 Transgenic Mouse Model for Extraosseous Plasmacytoma", PNAS 99(3):1509-1514 (Feb. 5, 2002).
Lemay L.G. et al., "Role of Interleukin 6 in Fever in Rats", Regulatory Integrative Comp. Physiol. 27:R798-R803 (1990).
Maione D. et al., "Coexpression of IL-6 and Soluble IL-6R Causes Nodular Regenerative Hyperplasia and Adenomas of the Liver", The EMBO Journal 17(19):5588-5597 (1998).
Murphy, D., MFA: the turducken of alleles*, a 76-slide PowerPoint® presentation that was used in conjunction with an oral presentation by Dr. Murphy that was given as a lecture at the Wellcome Trust Course: Genetic Manipulation of ES Cells at the Wellcome Trust, Hinxton, Cambridge, UK, in Nov. 2010.
Murphy, D., BAC-based Modifications of the Mouse Genome: The Big and the Backward, a 58-slide PowerPoint® presentation that was used in conjunction with an oral presentation by Dr. Murphy that was given as a lecture at the Wellcome Trust Advanced Course: Genetic Manipulation of ES Cells at the Wellcome Trust, Hinxton, Cambridge, UK on Nov. 3, 2009.
Naka T. et al., "The Paradigm of IL-6: From Basic Science to Medicine", Arthritis Res 4(Suppl 3):S233-S242 (2002).
Niemann H. et al., "Transgenic Farm Animals: Present and Future", Rev. Sci. Tech. Off. Int. Epiz. 24(1):285-298 (2005).
Northemann W. et al., "Structure of the Rat Interleukin 6 Gene and its Expression in Macrophage-Derived Cells", The Journal of Biological Chemistry 264(27):16072-16082 (Sep. 25, 1989).
Peters M. et al., "The Function of the Soluble Interleukin 6 (IL-6) Receptor In Vivo: Sensitization of Human Soluble IL-6 Receptor Transgenic Mice Towards IL-6 and Prolongation of the Plasma Half-Life of IL-6", J. Exp. Med. 183:1399-1406 (Apr. 1996).
Prelle K. et al., "Pluripotent Stem Cells-Model of Embryonic Development, Tool for Gene Targeting, and Basis of Cell Therapy", Anat. Histol. Embryol. 31:169-189 (2002).
Rongvaux A. et al., "Human Thrombopoietin Knockin Mice Efficiently Support Human Hematopoiesis In Vivo", PNAS 108(6):2378-2383 (Feb. 8, 2011).
Sawamura D. et al., "Induction of Keratinocyte Proliferation and Lymphocytic Infiltration by In Vivo Introduction of the IL-6 Gene into Keratinocytes and Possibility of Keratinocyte Gene Therapy for Inflammatory Skin Diseases Using IL-6 Mutant Genes", The Journal of Immunology 161:5633-5639 (1998).
Suematsu S. et al, "Generation of Plasmacytomas With the Chromosomal Translocation t(12;15) in Interleukin 6 Transgenic Mice", Proc. Natl. Acad. Sci. USA 89:232-235 (Jan. 1992).
Suematsu S. et al., "IgG1 Plasmacytosis in Interleukin 6 Transgenic Mice", Proc. Natl. Acad. Sci. USA 86:7547-7551 (Oct. 1989).

(56) References Cited

OTHER PUBLICATIONS

Sugita T. et al., "Functional Murine Interleukin 6 Receptor With the Intracisternal a Particle Gene Product at its Cytoplasmic Domain", J. Exp. Med. 171:2001-2009 (Jun. 1990).

Tanabe O. et al., "Genomic Structure of the Murine IL-6 Gene High Degree Conservation of Potential Regulatory Sequences Between Mouse and Human", The Journal of Immunology 141(11):3875-3881 (Dec. 1, 1988).

Tong C. et al., "Production of p53 Gene Knockout Rats by Homologous Recombination in Embryonic Stem Cells", Nature 467:211-215 (Sep. 9, 2011).

Tsantikos E. et al., "Autoimmune Disease in Lyn-Deficient Mice is Dependent on an Inflammatory Environment Established by IL-6", The Journal of Immunology 184:1348-1360 (2010).

Tsujinaka T. et al., "Interleukin 6 Receptor Antibody Inhibits Muscle Atrophy and Modulates Proteolytic Systems in Interleukin 6 Transgenic Mice", J. Clin. Invest. 97(1):244-249 (Jan. 1, 1996).

Tsujinaka T. et al, "Muscle Undergoes Atrophy in Association With Increase of Lysosomal Cathepsin Activity in Interleukin-6 Transgenic Mouse", Biochemical and Biophysical Research Communications 207(1):168-174 (Feb. 6, 1995).

Ueda O. et al., "Novel Genetically-Humanized Mouse Model Established to Evaluate Efficacy of Therapeutic Agents to Human Interleukin-6 Receptor", Scientific Reports 3(1196):1-8 (2013).

Weissenbach J. et al., "Two Interferon mRNAs in Human Fibroblasts: In Vitro Translation and *Escherichia coli* Cloning Studies", Proc. Natl. Acad. Sci. USA 77(12):7152-7156 (Dec. 1980).

Wheeler M.B. et al., "Transgenic Technology and Applications in Swine", Theriogenology 56:1345-1369 (2001).

Willinger T. et al., "Improving Human Hemato-Lymphoid System Mice by Cytokine Knock-in Gene Replacement", Trends in Immunology 32(7):321-327 (Jul. 2011).

Willinger T. et al., "Human IL-3/GM-CSF Knock-in Mice Support Human Alveolar Macrophage Development and Human Immune Responses in the Lung", PNAS 108(6):2390-2395 (Feb. 8, 2011).

Woodroofe C. et al., "Long-Term Consequences of Interleukin-6 Overexpression in Transgenic Mice", DNA and Cell Biology 11(8):587-591 (1992).

Yamasaki K. et al., "Cloning and Expression of the Human Interleukin-6 (BSF-2/IFNB 2) Receptor", Science 241:825-828 (Aug. 12, 1988).

Yasukawa K. et al., "Structure and Expression of Human B Cell Stimulatory Factor-2 (BSF-2/IL-6) Gene", The EMBO Journal 6(10):2939-2945 (1987).

Zhou H. et al., "Developing tTA Transgenic Rates for Inducible and Reversible Gene Expression", International Journal of Biological Sciences 5(2):171-181 (2009).

Chen H., Progress of Medical Bioengineering, People's Military Medical Press, p. 371 (Jul. 2004), together with an English-language abstract.

Chinese Office Action dated Jun. 3, 2021 received in Chinese Application No. 201810620759.8, together with an English-language translation.

Chinese Search Report dated Jun. 3, 2021 received in Chinese Application No. 201810620759.8, together with an English-language translation.

HUMANIZED IL-6 AND IL-6 RECEPTOR

CROSS REFERENCE TO RELATED APPLICATIONS

This application is a continuation of U.S. patent application Ser. No. 16/001,074, filed Jun. 6, 2018, now U.S. Pat. No. 10,433,528, which is a continuation of U.S. patent application Ser. No. 15/350,739, filed Nov. 14, 2016, now U.S. Pat. No. 10,004,211, which is a continuation of U.S. patent application Ser. No. 15/177,582, filed Jun. 9, 2016, now U.S. Pat. No. 9,622,460, which is a divisional of U.S. patent application Ser. No. 14/735,710, filed Jun. 10, 2015, now U.S. Pat. No. 9,392,777, which is a continuation of U.S. patent application Ser. No. 14/490,877, filed Sep. 19, 2014, now U.S. Pat. No. 9,078,418, which is a continuation of U.S. patent application Ser. No. 13/662,880, filed Oct. 29, 2012, now U.S. Pat. No. 8,878,001, which claims the benefit under 35 USC § 119(e) of U.S. Provisional Patent Application Ser. No. 61/556,579, filed on Nov. 7, 2011 and U.S. Provisional Patent Application Ser. No. 61/552,900, filed on Oct. 28, 2011; each provisional application is hereby incorporated by reference.

FIELD OF INVENTION

Non-human animals having a replacement of the endogenous non-human animal IL-6 and/or IL-6 receptor genes are provided. IL-6 and/or IL-6 receptor genes of the non-human animal are replaced, at the endogenous non-human loci, with human IL-6 and/or humanized IL-6 receptor genes comprising human sequence. Non-human animals that have human IL-6 and/or humanized IL-6 receptor genes, wherein the non-human animals do not exhibit one or more pathologies that are characteristic of non-human animals transgenic for human IL-6.

BACKGROUND

Mice transgenic for a human IL-6 gene are known in the art. However, random insertion of a human IL-6 transgene into the mouse genome results in poorly regulated expression of the human IL-6 protein, which manifests itself in a variety of pathologies in such transgenic mice, including, but not limited to, plasmacytosis and glomerulonephritis. As a result, these mice have limited usefulness.

There is a need for non-human animals, e.g., mice and rats, the express human or humanized IL-6 and/or human or humanized IL-6 receptor. There is a need for such humanized mice that do not exhibit one or more pathologies exhibited by transgenic hIL-6 mice.

SUMMARY

In one aspect, genetically modified non-human animals are provided that comprise a replacement at an endogenous IL-6 and/or IL-6 receptor locus of a gene encoding an endogenous IL-6 and/or IL-6 receptor with a gene encoding a human or humanized IL-6 and/or IL-6 receptor. Murine animals are provided that comprise a replacement of an endogenous IL-6 gene, at an endogenous murine IL-6 locus, with a human IL-6 gene; and/or that comprise a replacement of an endogenous IL-6 receptor gene (or nucleotide sequence encoding an ectodomain thereof) with a human IL-6 receptor gene (or nucleotide sequence encoding an ectodomain thereof).

In one aspect, genetically modified murine animals are provided that express a human IL-6 gene under the control of endogenous murine promoter and/or endogenous murine regulatory elements, from an endogenous murine IL-6 locus.

In one aspect, genetically modified murine animals are provided that express a human IL-6 receptor gene (or a gene encoding a human ectodomain and mouse transmembrane and intracellular domains) under the control of endogenous murine promoter and/or endogenous murine regulatory elements, from an endogenous murine IL-6 receptor locus.

In one aspect, a genetically modified animal (e.g., a murine animal, e.g., a mouse or rat) is provided that expresses a human IL-6 protein, wherein the non-human animal does not exhibit a pathology selected from plasmacytosis, glomerulonephritis, glomerulosclerosis, mesangioproliferative glomerulonephritis, intestinal lymphoma, kidney lymphoma, splenomegaly, lymph node enlargement, liver enlargement, megakaryocytes in bone marrow, compacted abnormal plasma cells, infiltration of plasma cells into lung or liver or kidney, mesangial cell proliferation in kidney, cerebral overexpression of IL-6, ramified microglial cells in white matter, reactive astrocytosis in brain, kidney failure, elevated megakaryocytes in spleen, muscle wasting (e.g., gastrocnemius muscle wasting), elevated muscle cathepsins B and B+L (e.g., around 20-fold and 6-fold), and a combination thereof.

In one embodiment, the non-human animal comprises a normal B cell population. In one embodiment, the normal B cell population is approximately the same in number and immunophenotype as a wild-type animal, e.g., a wild-type mouse.

In one embodiment, the non-human animal is murine (e.g., a mouse or rat) and expresses human IL-6 (hIL-6) in serum at a level below about 800 pg/mL, below about 700, 600, 500, 400, 300, or 200 pg/mL. In a specific embodiment, the murine animal expresses hIL-6 in serum at a level of about 50 to about no more than 200 pg/mL, in another embodiment about 75-125 pg/mL, in another embodiment at about 100 pg/mL.

In one aspect, a non-human animal is provided that expresses hIL-6 and/or hIL-6R, wherein the non-human animal expresses hIL-6 and/or hIL-6R from an endogenous non-human IL-6 locus and/or an endogenous non-human hIL-6R locus. In a specific embodiment, the non-human animal is murine (e.g., mouse or rat).

In one aspect, a genetically modified mouse is provided that expresses hIL-6 from an endogenous mouse IL-6 locus, wherein the endogenous mouse IL-6 gene has been replaced with a hIL-6 gene.

In one embodiment, the mouse comprises a cell that expresses an IL-6 receptor (IL-6R) that comprises a human ectodomain on the surface of the cell. In one embodiment, the cell is a lymphocyte. In one embodiment, the lymphocyte is a B cell.

In one embodiment, about 6.8 kb at the endogenous mouse IL-6 locus, including exons 1 through 5 and a 3' untranslated sequence, is deleted and replaced with about 4.8 kb of human IL-6 gene sequence comprising exons 1 through 5 of the human IL-6 gene. In a specific embodiment, the human IL-6 gene comprises exons 1 through 5 of the human IL-6 gene of human BAC CTD-2369M23.

In one aspect, a genetically modified mouse is provided that expresses IL-6 from a human IL-6 gene, wherein the mouse expresses human IL-6 in its serum.

In one embodiment, the mouse serum exhibits a serum concentration of human IL-6 of about 25 to about 300 pg/mL, 50 to about 250 pg/mL, 75 to about 200 pg/mL, or 100 to about 150 pg/mL. In a specific embodiment, the level of human IL-6 in the serum of the mouse is about 100 pg/mL.

In one embodiment, the level of a pan B cell-specific marker in bone marrow of the mouse is about the same as that of a wild-type mouse. In one embodiment, the level of a pan B cell-specific marker in spleen is about the same as that of a wild-type mouse. In one embodiment, the pan B cell-specific marker is selected from B220, CD19, CD20, CD22, CD79a, CD79b, L26, and Pax-5 (BSAP).

In one aspect, a genetically modified mouse is provided that expresses hIL6, wherein the mouse does not exhibit a feature selected from plasmacytosis, splenomegaly, lymph node enlargement, compacted abnormal plasma cells, and a combination thereof.

In one embodiment, the mouse comprises a spleen that is about the same weight (per body weight) as a wild-type mouse. In one embodiment, the lymph nodes of the mouse are about the same weight (per body weight) as a wild-type mouse. In one embodiment, plasma cells of the mouse do not exhibit plasmocytosis characteristic of mice that overexpress human IL-6.

In one embodiment, the mouse does not exhibit glomerulonephritis.

In one embodiment, the mouse exhibits a mesangial cell level comparable to a wild-type mouse.

In one aspect, a genetically modified mouse is provided that expresses hIL6 from an endogenous mouse IL-6 locus, wherein the endogenous mouse IL-6 gene has been replaced with a hIL-6 gene, wherein the mouse does not exhibit a feature selected from a morphologically detectable neuropathology, a reactive astrocytosis, and a combination thereof. In one embodiment, the mouse comprises a brain that is morphologically indistinct from a wild-type mouse brain. In one embodiment, the mouse comprises brain tissue that exhibits a level of reactive astrocytosis that is no higher than that of a wild-type mouse.

In one embodiment, the mouse does not express human IL-6 in neurons. In one embodiment, the mouse comprises activated astrocyte levels that are comparable to activated astrocyte levels in a wild-type mouse.

In one embodiment, the mouse comprises ramified microglial cells in its white matter, wherein the ramified microglial cells are present in an amount equivalent to an amount of ramified microglial cells in a wild-type mouse.

In one embodiment, the mouse does not exhibit a reactive atrocytosis. In one embodiment, the white matter of the mouse is morphologically indistinct from the white matter of a wild-type mouse. In one embodiment, the white matter of the mouse is histologically indistinct from a wild-type mouse white matter with respect to histochemical staining of reactive astrocytes.

In one embodiment, the mouse comprises a brain that is morphologically indistinct from a wild-type mouse brain. In one embodiment, the mouse comprises brain tissue that exhibits a level of reactive astrocytosis that is no higher than that of a wild-type mouse.

In one aspect, a genetically modified mouse is provided that expresses hIL6 from an endogenous mouse IL-6 locus, wherein the endogenous mouse IL-6 gene has been replaced with a hIL-6 gene, wherein the mouse does not exhibit a feature selected from a life span shortened by about 50% or more, kidney failure, hypergammaglobulinemia, elevated megakaryocytes in spleen, elevated megakaryocytes in bone marrow, plasmacytosis of spleen, plasmacytosis of thymus, plasmacytosis of lymph nodes, glomerulonephritis, glomerulosclerosis, and a combination thereof.

In one embodiment, the mice have a life span that exceeds 20 weeks. In one embodiment, the mice have a life span that exceeds 30 weeks, 40 weeks, or 50 weeks. In one embodiment, the mice exhibit a life span about equal to that of a wild-type mouse of the same strain.

In one embodiment, the mice exhibit a level of megakaryocytes in spleen that is no more than about the splenic megakaryocyte level of a wild-type mouse In one embodiment, the mice comprise lymphoid organs that are essentially devoid of abnormal and compactly arranged plasmacytoid cells.

In one embodiment, the mice exhibit gamma globulin serum levels equivalent to gamma globulin serum levels in wild-type mice. In one embodiment, the levels of α1- and β-globulin in serum of the mice are equivalent to α1- and β-globulin serum levels of wild-type mice of the same strain.

In one aspect, a genetically modified mouse is provided that expresses human IL-6 from an endogenous mouse IL-6 locus, wherein the endogenous mouse IL-6 gene has been replaced with a hIL-6 gene, wherein the mouse does not exhibit a feature selected from muscle wasting, an elevated cathepsin B level as compared with a wild-type mouse of the same strain, an elevated cathepsin A+B level as compared with a wild-type mouse of the same strain, an increased liver weight as compared with a wild-type mouse of the same strain, and a combination thereof.

In one embodiment, the weight of the liver of the mouse is about 800-900 mg at 12 weeks.

In one embodiment, the mouse exhibits a cathepsin B level throughout its life span that is no more than about the level observed in a wild-type mouse. In one embodiment, the mouse exhibits a cathepsin A+B level throughout its life span that is no more than about the level observed in a wild-type mouse.

In one embodiment, the mouse as an adult exhibits a gastrocnemus muscle weight that is within about 10% of the weight of a wild-type mouse of the same strain. In one embodiment, the mouse as an adult exhibits a gastrocnemus muscle weight that is about the same as that of a wild-type mouse.

In one aspect a mouse is provided that comprises a nucleotide sequence encoding a human IL-6 protein, wherein the nucleotide sequence encoding the human IL-6 protein replaces in whole or in part an endogenous nucleotide sequence encoding and endogenous mouse IL-6 protein.

In one aspect, a mouse is provided that comprises a replacement at an endogenous mouse IL-6 receptor locus of mouse IL-6Rα ectodomain with an ectodomain sequence of a human IL-6Rα to form a chimeric human/mouse IL-6Rα gene.

In one embodiment, the chimeric IL-6Rα gene is under the control of a mouse promoter and/or mouse regulatory elements at the endogenous mouse IL-6Rα locus.

In one embodiment, about 35.4 kb of mouse IL-6Rα ectodomain-encoding sequence is replaced with about 45.5 kb of human IL-6R ectodomain-encoding sequence.

In one embodiment, the human IL-6R ectodomain-encoding sequence encompasses the first (ATG) codon in exon 1 through exon 8.

In one embodiment, the mouse IL-6Rα sequence that is replaced includes a contiguous sequence that encompasses exons 1 through 8. In a specific embodiment, exons 1 through 8 and a portion of intron 8 is deleted.

In one aspect, a genetically modified mouse is provided, comprising a replacement at an endogenous mouse IL-6 locus of a mouse gene encoding IL-6 with a human gene encoding human IL-6, wherein the human gene encoding human IL-6 is under control of endogenous mouse regulatory elements at the endogenous mouse IL-6 locus.

In one embodiment, the human gene encoding human IL-6 is a human IL-6 gene of BAC ID CTD-2369M23.

In one embodiment, the mouse expresses a mouse IL-6Rα. In one embodiment, the mouse expresses a human IL-6Rα. In one embodiment, the humanized IL-6Rα comprises a human ectodomain. In one embodiment, the humanized IL-6Rα comprises a mouse transmembrane domain and a mouse cytoplasmic domain. In one embodiment, the mouse expresses a humanized IL-6Rα that comprises a humanization of ectodomain but not transmembrane and/or cytosolic domain.

In one embodiment, the mouse does not exhibit a feature selected from plasmocytosis, glomerulosclerosis, glomerulonephritis, kidney failure, hypergammaglobulinemia, elevated megakaryocytes in spleen, elevated megakaryocytes in bone marrow, splenomegaly, lymph node enlargement, compacted abnormal plasma cells, and a combination thereof.

In one aspect, a genetically modified mouse is provided, comprising a humanization of an endogenous mouse IL-6Rα gene, wherein the humanization comprises a replacement of mouse IL-6Rα ectodomain-encoding sequence with human IL-6Rα ectodomain-encoding sequence at the endogenous mouse IL-6Rα locus.

In one embodiment, a contiguous mouse sequence comprising mouse exons 1 through 8 is replaced with a contiguous genomic fragment of human IL-6Rα sequence encoding a human IL-6Rα ectodomain. In one embodiment, the contiguous genomic fragment of human IL-6Rα sequence encoding the ectodomain is from BAC CTD-2192J23.

In one embodiment, the mouse further comprises a humanized IL-6 gene. In one embodiment, the mouse comprises a replacement at an endogenous mouse IL-6 locus of a mouse IL-6 gene with a human IL-6 gene. In one embodiment, the humanized IL-6 gene is under control of endogenous mouse regulatory elements.

In one aspect, a method is provided for making a humanized mouse, comprising replacing a mouse gene sequence encoding mouse IL-6 with a human gene encoding human IL-6.

In one embodiment, the replacement is at an endogenous mouse IL-6 locus, and the human gene encoding human IL-6 is operably linked to endogenous mouse regulatory sequences.

In one aspect, a method for making a humanized mouse is provided, comprising replacing mouse exons encoding ectodomain sequences of mouse IL-6Rα with a human genomic fragment encoding ectodomain sequences of human IL-6Rα to form a humanized IL-6Rα gene.

In one embodiment, the replacement is at an endogenous mouse IL-6Rα locus, and the humanized IL-6Rα gene is operably linked to endogenous mouse regulatory sequences.

In one aspect, a genetically modified mouse is provided, comprising a humanized IL-6Rα gene comprising a replacement of mouse ectodomain-encoding sequence with human ectodomain sequence, wherein the humanized IL-6Rα gene comprises a mouse transmembrane sequence and a mouse cytoplasmic sequence; wherein the mouse further comprises a gene encoding a human IL-6, wherein the gene encoding a human IL-6 is under control of endogenous mouse IL-6 regulatory elements.

In one embodiment, the mouse is incapable of expressing a fully mouse IL-6Rα and incapable of expressing a mouse IL-6.

In various aspects, the genetically modified mice described herein comprise the genetic modifications in their germline.

In one aspect, a tissue, cell, or membrane fragment from a mouse as described herein is provided.

In one embodiment, the tissue or cell is from a mouse that expresses a human IL-6 protein, but that does not express a mouse IL-6 protein. In one embodiment, the tissue or cell is from a mouse that expresses a humanized IL-6Rα protein, but not a mouse IL-6Rα protein. In one embodiment, the humanized IL-6Rα protein comprises a human ectodomain and a mouse transmembrane domain and a mouse cytosolic domain. In one embodiment, the tissue or cell is from a mouse that expresses a human IL-6, a humanized IL-6Rα, and that does not express a mouse IL-6 and does not express an IL-6Rα that comprises a mouse ectodomain.

In one aspect, an ex vivo complex of a mouse cell bearing a humanized IL-6Rα (human ectodomain and mouse transmembrane and mouse cytoplasmic domain) and a human IL-6 is provided.

In one aspect, a mouse embryo comprising a genetic modification as described herein is provided.

In one aspect, a mouse host embryo is provided that comprises a donor cell that comprises a genetic modification as described herein.

In one aspect, a pluripotent or totipotent non-human animal cell comprising a genetic modification as described herein is provided. In one embodiment, the cell is a murine cell. In one embodiment, the cell is an ES cell.

In one aspect, a mouse egg is provided, wherein the mouse egg comprises an ectopic mouse chromosome, wherein the ectopic mouse chromosome comprises a genetic modification as described herein.

In one aspect, the mouse, embryo, egg, or cell that is genetically modified to comprise a human IL-6 gene or human or humanized IL-6Rα gene is of a mouse that is of a C57BL strain selected from C57BL/A, C57BL/An, C57BLGrFa, C57BL/KaLwN, C57BL/6, C57BL/6J, C57BL/6ByJ, C57BL6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain.

In yet another embodiment, the mouse is a mix of a BALB strain and another aforementioned strain. In one embodiment, the mouse is Swiss or Swiss Webster mouse.

Each of the aspects and embodiments described herein are capable of being used together, unless excluded either explicitly or clearly from the context of the embodiment or aspect.

DETAILED DESCRIPTION

IL-6 and IL-6R

Figure 1:
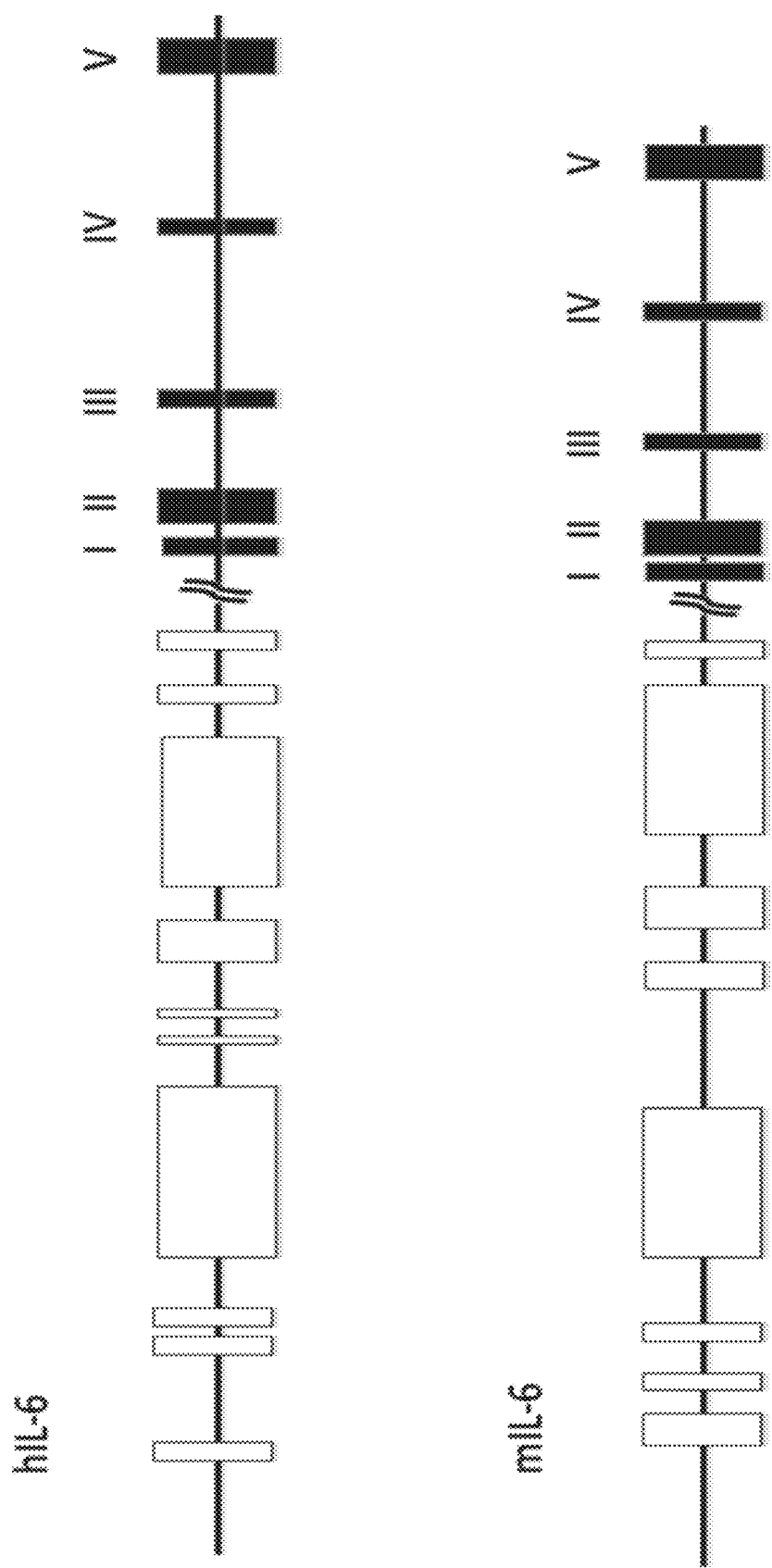
FIG. 1 provides an illustration, not to scale, of the human (A) and mouse (B) IL-6 genomic loci. Exons I, II, III, IV, and V (in both human and mouse) are indicated by closed boxes to the right in the figure. Selected putative regulatory regions are indicated by open boxes to the left in the figure.

The IL-6 receptor (IL-6R) was long characterized as a receptor for a B cell stimulatory factor (BSF-2, or B cell Stimulatory Factor 2; also, BCDF, or B Cell Differentiation Factor) responsible for inducing B cells to synthesize immunoglobulin (Yamasaki et al. (1988) Cloning and Expression of the Human Interleukin-6(BSF-2/IFN 2) Receptor, Science 241:825-828). IL-6 was first described as interferon-β2 as the result of its discovery during a search for a virally-induced protein termed interferon-β, by treating human fibroblasts with dsRNA poly(I)poly(C) to induce an antiviral response (Weissenbach et al. (1980) Two interferon mRNAs in human fibroblasts: In vitro translation and *Escherichia coli* cloning studies, Proc. Natl Acad. Sci. USA 77(12):7152-7156; Keller et al. (1996) Molecular and Cellular Biology of Interleukin-6 and Its Receptor, Frontiers in Bioscience 1:d340-357).

The human cDNA encodes a 468 amino acid protein having a 19-mer signal sequence and a cytoplasmic domain of about 82 amino acids that lacks a tyrosine kinase domain (see, Id.). The N-terminal (ectodomain) of the protein has an Ig superfamily domain of about 90 amino acids, a 250-amino acid domain between the Ig superfamily domain and the membrane, a transmembrane span of about 28 amino acids (see, Id.). The ectodomain of the receptor binds its ligand IL-6, which triggers association with gp130 in the membrane and it is this complex that conducts signal transduction; the cytoplasmic domain reportedly does not transduce signal (Taga et al. (1989) Interleukin-6 Triggers the Association of Its Receptor with a Possible Signal Transducer, gp130, Cell 58:573-581). Indeed, a soluble form of IL-6R lacking a cytoplasmic domain can associate with IL-6 and bind gp130 on the surface of a cell and effectively transduce signal (Id.).

The homology of hIL-6R and mIL-6R at the protein level is only about 54%; the transmembrane domain has a homology of about 79%, whereas the cytoplasmic domain has a homology of about 54% (Sugito et al. (1990)).

The natural ligand for the IL-6R, IL-6, was first isolated from cultures of HTLV-1-transformed T cells (see, Hirano et al. (1985) Purification to homogeneity and characterization of human B cell differentiation factor (BCDF or BSFp-2), Proc. Natl. Acad. Sci. USA 82:5490-5494). A human cDNA for the IL-6 gene was cloned at least twice, once as BSF-2 (see, Hirano et al. (1086) Complementary DNA for a novel human interleukin (BSF-2) that induces B lymphocytes to produce immunoglobulin, Nature 324:73-76) and once as IFNβ2 (see, Zilberstein et al. (1986) Structure and expression of cDNA and genes for human interferon-beta-2, a distinct species inducible by growth-stimulatory cytokines, EMBO 5:2529-2537), although it has since been demonstrated that recombinant human IL-6 exhibits no detectable IFN activity.

Human IL-6 is a 184-amino acid protein that exhibits only about 42% homology with mouse IL-6, although the genomic organization of the human and mouse genes are basically the same, and the promoter regions of the human and mouse genes share a 400-bp stretch that is highly conserved (see, Tanabe et al. (1988) Genomic Structure of the Murine IL-6 Gene: High Degree Conservation of Potential Regulatory Sequences between Mouse and Human, J. Immunol. 141(11):3875-3881).

The human IL-6 gene is about 5 kb (Yasukawa et al. (1987) Structure and expression of human B cell stimulatory factor-2 (BSC-2/IL-6) gene, EMBO J. 6(10):2939-2945), whereas the mouse IL-6 gene is about 7 kb (Tanabe et al. (1988) Genomic Structure of the Murine IL-6 Gene: High Degree Conservation of Potential Regulatory Sequences between Mouse and Human, J. Immunol. 141(11):3875-3881). The mouse and human IL-6 genes reportedly share highly conserved 5'-flanking sequence important to regulation. A schematic diagram of the human and mouse IL-6 genomic loci is shown in FIG. 1 (not to scale). Exons I, II, III, IV, and V (in both human and mouse) are indicated by closed boxes to the right in the figure. Selected putative regulatory regions are indicated by open boxes to the left in the figure. The putative regulatory regions for humans are, from left to right, a glucocorticoid element from −557 to −552; an IFN enhancer core sequence from −472 to −468; a glucocorticoid element from −466 to −461; an AT-rich region from −395 to −334, a consensus AP-1 binding site from −383 to −277; an IFN enhancer core sequence from −253 to −248; a GGAAA-containing motif from −205 to −192; a c-fos SRE homology sequence from −169 to −82 containing an IFN enhancer core sequence, a cAMP-response element, a GGAAA motif, a CCAAT box, and a GC-rich region; and AP-1 binding site from −61 to −55; and a CCAAT box from −34 to −30. The putative regulatory regions for mouse are, from left to right, a GC rich region from −553 to −536, a glucocorticoid element from −521 to −516 and from −500 to −495; a Z-DNA stretch from −447 to −396; an AP-1 binding site overlapping an IFN enhancer core sequence from −277 to −288, a GGAAA motif overlapping an IFN enhancer core sequence from −210 to −195; a c-fos SRE homology region from −171 to −82 containing a cAMP response element, a GGAAA motif overlapping an IFN enhancer core sequence, and a GC-rich region; and, an AP-1 binding site from −61 to −55. Mouse codons I-V have lengths 19, 185, 114, 150, and 165, respectively. Mouse intron lengths are: I-III, 162 bp; II-III, 1253 bp; III-IV, 2981 bp; IV-V, 1281 bp. Human codons I-V have lengths 19, 191, 114, 147, and 165. Human intron lengths are I-II, 154; II-III, 1047; III-IV, 706; IV-V, 1737. Genomic organization data are from Tanabe et al. (1988), and Yasukawa et al. (1987) Structure and expression of human B cell stimulatory factor-2 (BSF-2/IL-6) gene, EMBO J. 9(10):2939-2945.

It might be reasonable to presume that the mouse and human IL-6 genes appear to be similarly regulated based on the similarity of their 5'-flanking sequence. A variety cell types exhibit enhanced IL-6 expression in response to IL-1, TNF, PDGF, IFN, serum, poly(I)poly(C), and cycloheximide (see, Tanabe et al. (1988). IL-6 in humans mediates the acute phase response, hematopoiesis, B cell differentiation, T cell activation, growth and/or differentiation and/or activation of a variety of cell types (e.g., hepatocytes, fibroblasts, endothelial cells, neurons, pituitary cells, lymphomas, myelomas, breast carcinomas, NK cells, macrophages, osteoclasts, etc.) (reviewed in, e.g., Heinrich et al. (1990), Kishimoto et al. (1989), and Keller et al. (1996); Sugita et al. (1990) Functional Murine Interleukin Receptor with Intracistemal A Particle Gene Product at its Cytoplasmic Domain, J. Exp. Med. 171:2001-2009).

In practice, however, mice transgenic for human IL-6 exhibit a panoply of substantial and debilitating pathologies, reflecting a significant pleiotropy of the IL-6 gene. Transgenic mice comprising a 6.6-kb fragment containing the human IL-6 gene and a µ enhancer (Ep) produce high concentrations of hIL-6 and extremely high IgG1 levels (120- to 400-fold over wild-type mice), reflecting an IL-6 deregulation that is accompanied by plasmacytosis, mesangio-proliferative glomerulonephritis, and high bone marrow megakaryocyte levels (Suematsu et al. (1989) IgG1 plasmacytosis in interleukin 6 transgenic mice, Proc. Natl Acad. Sci. USA 86:7547-7551). Aberrant regulation of IL-6 and/or IL-6R is associated with myelomas, plastocytomas, rheumatoid arthritis, Castleman's disease, mesangial proliferative glomerulonephritis, cardiac myxoma, plams cell neoplasias, psoriasis, and other disorders (see, Kishimoto, T. (1989) The Biology of Interleukin-6, Blood 74(1):1-10; Sugita et al. (1990); also, Hirano et al. (1990) Biological and clinical aspects of interleukin 6, Immunology Today 11(12): 443-449)). IL-6 is also implicated in sustaining levels of intra-prostatic androgens during androgen deprivation treatment of prostate cancer patients by a paracrine and/or autocrine mechanism, potentially providing castration-resistant prostate tumor growth (Chun et al. (2009) Interleukin-6 Regulates Androgen Synthesis in Prostate Cancer Cells, Clin. Cancer Res. 15:4815-4822).

The human protein is encoded as a 212 amino acid protein, in mature form a 184 amino acid protein following cleavage of a 28 amino acid signal sequence. It contains two N-glycosylation and two O-glycosylation sites, and human IL-6 is phosphorylated in some cells. The mouse protein is encoded as a 211 amino acid protein, in mature form a 187 amino acid protein following cleavage of a 23 amino acid signal sequence. O-glycosylation sites are present, but not N-glycosylation sites. (See reviews on IL-6, e.g., Heinrich et al. (1990) Interleukin-6 and the acute phase response, Biochem. J. 265:621-636.)

IL-6 function is pleiotropic. The IL-6 receptor is found on activated B cells but reportedly not on resting B cells. In contrast, IL-6R is found on resting T cells and can reportedly promote T cell differentiation, activation, and proliferation, including the differentiation of T cells into cytotoxic T lymphocytes in the presence of IL-2.

Humanized IL-6/IL-6R Ectodomain Mice and IL-6-Mediated Acute Phase Response

In humans, IL-6 induces the acute phase response. Early studies with human hepatocytes established that IL-6 induces acute phase proteins such as, e.g., C-reactive protein (CRP) and serum amyloid A (SAA) in a dose-dependent and time-dependent manner (reviewed in Heinrich et al. (1990) Interleukin-6 and the acute phase response, Biochem. J. 265:621-636). Non-human animals, e.g., mice or rats, comprising humanized IL-6 and IL-6R genes are therefore useful systems for measuring the acute phase response mediated by human IL-6. Such animals are also useful for determining whether a substance induces an IL-6-mediated acute phase response, by exposing a humanized IL-6/IL-6R animal as described herein to the substance, and measuring a level of one or more acute phase response proteins (or RNAs). In one embodiment, the humanized animal is exposed to the substance in the presence of an antagonist of a human IL-6R, and a level of one or more acute phase response proteins (or RNAs) is measured, wherein a reduction in a level of an acute phase response protein (or RNA) in the presence of the human IL-6R antagonist indicates a human IL-6R-mediated acute phase response.

Human IL-6 can bind both human IL-6R and mouse IL-6R; mouse IL-6 binds mouse IL-6R but not human IL-6R (no binding of mIL-6 to hIL-6R detectable, whereas hIL-6 can compete with mIL-6 for binding mIL-6R; Coulie et al. (1989) High- and low-affinity receptors for murine interleukin 6. Distinct distribution on B and T cells, Eur. J. Immunol. 19:2107-211); see also, e.g., Peters et al. (1996) The Function of the Soluble Interleukin 6 (IL-6) Receptor In Vivo: Sensitization of Human Soluble IL-6 Receptor Transgenic Mice Towards IL-6 and Prolongation of the Plasma Half-life of IL-6, J. Exp. Med. 183:1399-1406). Thus, human cells that bear hIL-6R in a mouse (e.g., in a xenogenic transplant) cannot rely on endogenous mIL-6 to carry out IL-6-mediated functions, including but not limited to the role of IL-6 blood cell or lymphocyte development (e.g., hematopoiesis, B cell activation, T cell activation, etc.).

In a mixed in vivo system comprising a wild-type mouse IL-6 gene and a human IL-6R gene (but no mouse IL-6R gene), an acute phase response inducer is not expected to induce detectable levels of acute phase proteins that would indicate an acute phase response. However, a humanized mouse as described herein, comprising a humanized IL-6 gene and an IL-6R gene comprising a humanized ectodomain sequence will respond to an acute phase response inducer and exhibit acute phase response proteins in serum.

Figure 2:
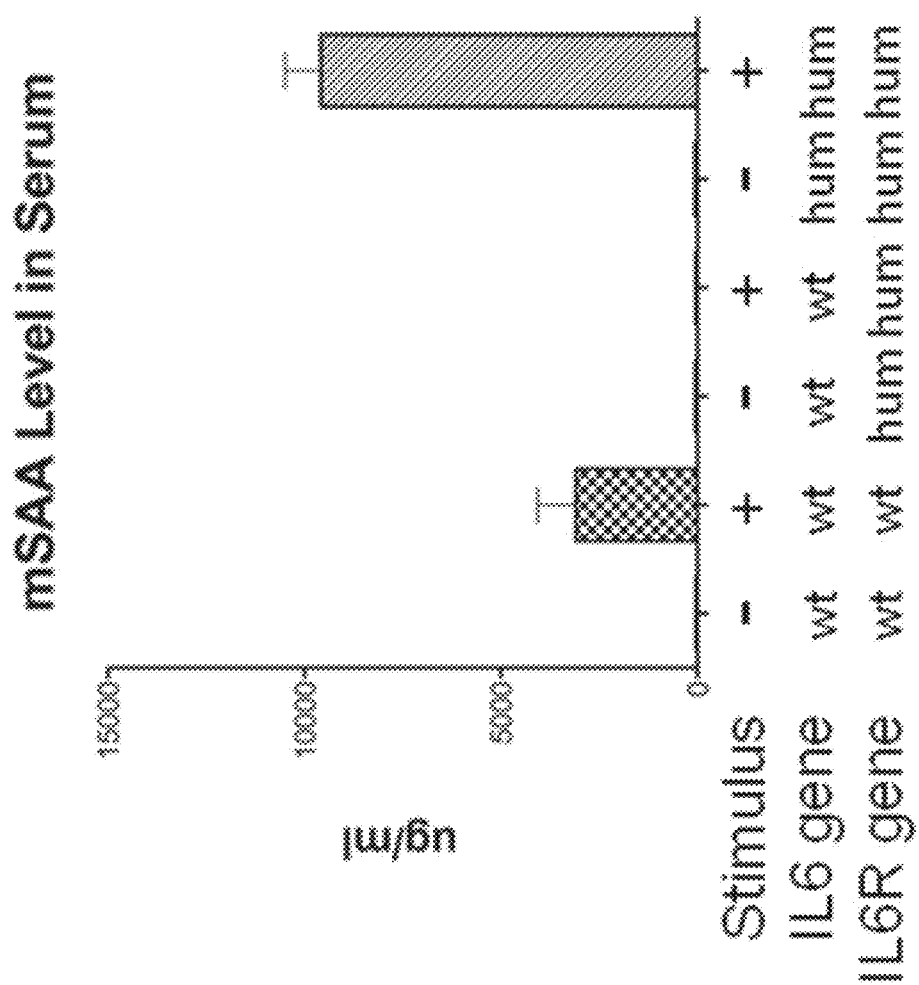
FIG. 2 shows acute phase response (mSAA level) in the presence or absence of turpentine in wild-type mice, humanized ectodomain IL-6R mice, and mice with humanized IL-6 and IL-6R genes.
Figure 3:
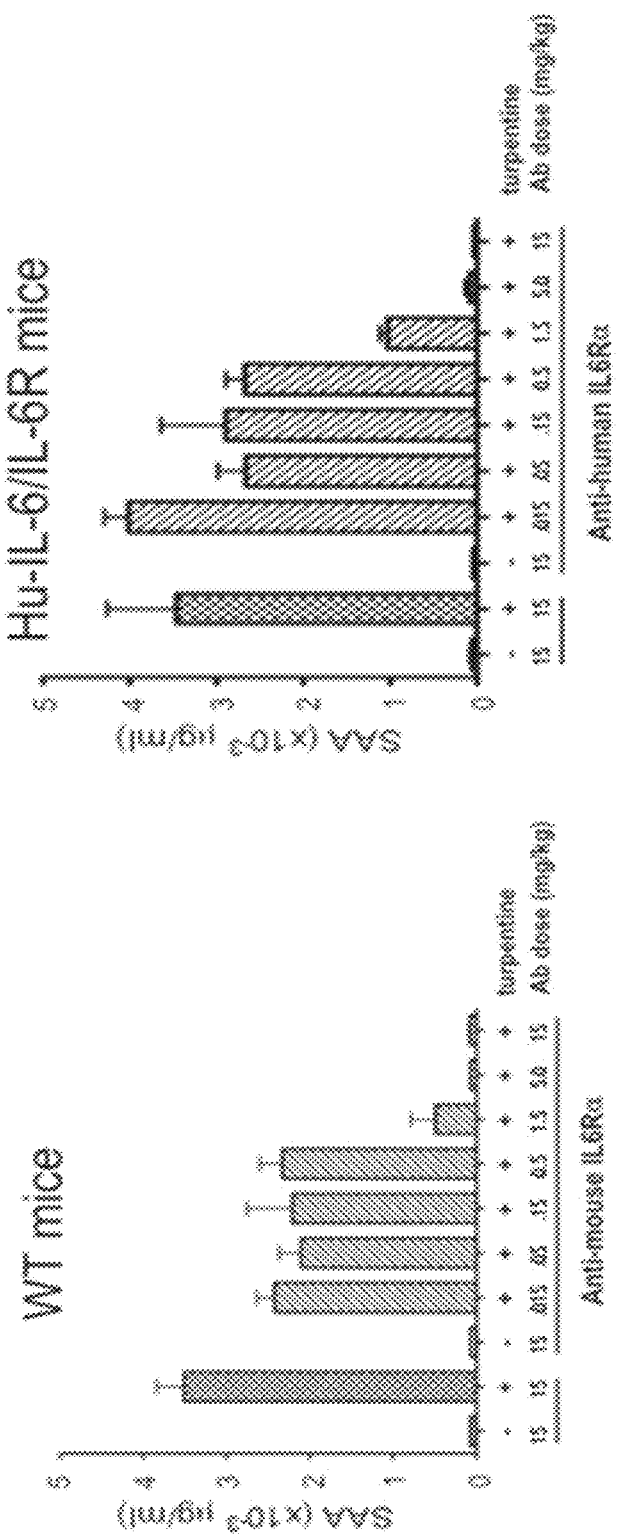
FIG. 3 shows turpentine-dependent acute phase response (SAA) in wild-type mice the absence or presence of anti-mouse IL-6R antibody (A); and turpentine-dependent acute phase response in humanized IL-6/IL-6R mice in the absence or present of anti-human IL-6R antibody (B).

Mice wild-type for IL-6/IL-6R tested for acute phase proteins in the presence or absence of the acute phase inducer turpentine showed a turpentine-dependent increase in acute phase proteins. Mice with humanized IL-6 gene, but not IL-6R, showed no acute phase response in the presence of turpentine. But mice bearing both a human IL-6 gene and an IL-6R gene with a humanized ectodomain exhibited a strong acute phase response (FIG. 2). The IL-6-mediated acute phase response was IL-6 dependent in both wild-type mice (FIG. 3, top) and in humanized IL-6/IL-6R ectodomain mice (FIG. 3, bottom), as evidenced by the ability of the appropriate anti-IL-6R antibody to abrogate the acute phase response at a sufficiently high antibody dose. Thus, a double humanization of IL-6 and IL-6R recapitulates the wild-type IL-6-mediated acute phase response with respect to serum acute phase proteins.

Genetically Modified Mice

Genetically modified mice are provided that express a human IL-6 and/or a humanized IL-6 receptor from endogenous mouse loci, wherein the endogenous mouse IL-6 gene and/or the endogenous mouse IL-6 receptor gene have been replaced with a human IL-6 gene and/or a human sequence comprising a sequence that encodes an ectodomain of a human IL-6 receptor. The genetically modified mice express the human IL-6 and/or humanized IL-6 receptor from humanized endogenous loci that are under control of mouse promoters and/or mouse regulatory elements. The replacement(s) at the endogenous mouse loci provide non-human animals that express human IL-6 and a humanized IL-6 receptor in a manner that does not result in the panoply of substantial pathologies observed in IL-6 transgenic mice known in the art.

Transgenic mice that express human IL-6 are known in the art. However, they generally suffer from significant pathologies that severely limit their usefulness. Humanized mice as described herein express a human IL-6 and/or humanized IL-6 receptor under the control of endogenous mouse regulatory elements at endogenous mouse IL-6 and IL-6Rα loci. These mice, in contrast, exhibit expression patterns with respect to these genes that are different from transgenic mice known in the art.

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene no matter where in the animal's genome the transgene winds up. But in many cases the transgene with human regulatory elements expresses in a manner that is unphysiological or otherwise unsatisfactory, and can be actually detrimental to the animal. In contrast, the inventors demonstrate that a replacement with human sequence at an endogenous locus under control of endogenous regulatory elements provides a physiologically appropriate expression pattern and level that results in a useful humanized animal whose physiology with respect to the replaced gene are meaningful and appropriate and context of the humanized animars physiology.

Fertilized mouse eggs injected with a construct having the MHC class I promoter H2 and a β-globin intron driving expression of a 695-bp mouse IL-6 gene reportedly produce mice that constitutively express mouse IL-6 at relatively high levels (as compared with wild-type mice) (see, Woodrofe et al. (1992) Long-Term Consequences of Interleukin-6 Overexpression in Transgenic Mice, DNA and Cell Biology 11 (8):587-592). But these mice are prone to develop lymphomas associated with the intestines, lymph nodes, and kidney, as well as splenic amyloid deposits. They also exhibit abnormal B cell maturation (see, Woodrofe et al., Id.), so that studies of B cell function are compromised. In contrast, mice as described herein that comprise a replacement of the mouse IL-6 gene with a human IL-6 gene at the mouse IL-6 locus are not prone to develop these lymphomas, and the mice exhibit apparently normal B cell populations.

Mice (C57BL/6) transgenic for hIL-6 due to a random insertion of a 6.6-kb (BamHI-Pvu II fragment) length of human DNA containing the hIL-6 gene coupled with an IgM enhancer have been reported (see, Suematsu et al. (1989) IgG1 plasmocytosis in interleukin 6 transgenic mice, Proc. Natl. Acad. Sci. USA 86:7547-7551). The mice express hIL-6 at between 800 pg/mL and 20,000 pg/mL in serum, where wild-type mice typically express only about 100 pg/mL IL-6. The mice exhibit an increase in serum Ig (120 to 400-fold over wild-type mice) and a decrease in albumin as they age. The mice suffer from a massive plasmacytosis, exhibit splenomegaly and lymph node enlargement, as well as exhibiting plasma cells and increased megakaryocytes in bone marrow. Upon inspection, what appear to be enlarged lymph nodes are instead massed of compacted abnormal plasma cells. Both spleen and thymus exhibit massive proliferation of plasma cells, which also infiltrate portions of the lung, liver, and kidney. Kidney in these mice also exhibits IL-6-stimulated mesangial cell proliferation typical of mesangio-proliferative glomerulonephritis. Similarly, mice (BALB/c) transgenic for a trimmed hIL-6 cDNA driven by a mouse H-2L$^d$ promoter randomly inserted into the genome display severe plasmacytosis (see, Suematsu et al. (1992) Generation of plasmacytomas with the chromosomal translocation t(12;15) in interleukin 6 transgenic mice, Proc. Natl. Acad. Sci. USA 89:232-235). Although C57BL/6 mice that overexpress hIL-6 do not develop transplantable plasmacytomas (they do exhibit plasmacytosis), transgenic BL/6 mice back-crossed into BALB/c mice reportedly do.

Random transgenesis of a hIL-6 cDNA driven by a glial fibrillary acidic protein (GFAP) gene promoter reportedly results in hIL-6 overexpression in the mouse central nervous system, which also leads to significant pathologies (see, Campbell et al. (1993) Neurologic disease induced in transgenic mice by cerebral overexpression of interleukin 6, Proc. Natl. Acad. Sci. USA 90:10061-10065). These mice exhibit extensive neuropathology and reactive astrocytosis resulting from IL-6 expression in the CNS due to loss of control as the result of random integration of an IL-6 transgene at an apparently CNS-permissive transcriptional locus. Although expression of hIL-6 cDNA linked to a β-globin 3'-UTR and driven by a neuron-specific enolase promoter microinjected into fertilized mouse eggs (F1 C57BL/6×BALB/c) produced mice with a normal lifespan and without apparent neurological defects that expressed hIL-6 in neurons but not elsewhere (see, Fattor et al. (1994) IL-6 Expression in Neurons of Transgenic Mice Causes Reactive Astrocytosis and Increase in Ramified Microglial Cells But No Neuronal Damage, Eur. J. Neuroscience 7:2441-2449), the mice exhibited high levels (20- to 30-fold higher than wild-type) of activated and enlarged astrocytes with increased processes throughout the brain, as well as a 10- to 15-fold increase in ramified microglial cells in white matter. Thus, brain expression of IL-6 reportedly leads to conditions that range from reactive astrocytosis to frank and profound neuropathology.

Microinjection into fertilized eggs of an F1 cross of C57BL/6×"DBAII" mice of a 639-bp hIL-6 cDNA linked to a β-globin 3'-UTR and a mouse MT-1 promoter reportedly produced a transgenic mouse in which the hIL-6 gene was randomly integrated produced a weakened and diseased mouse that dies young of kidney failure (see Fattori et al. (1994) Blood, Development of Progressive Kidney Damage and Myeloma Kidney in Interleukin-6 Transgenic Mice, Blood 63(9):2570-2579). Transgenic mice expired at 12-20 weeks and exhibited elevated levels of al and β-globulins in plasma, hypergammaglobulinemia, elevated megakaryocytes in spleen (3-fold higher than wild-type) and bone marrow, plasmacytosis of lymphoid organs (spleen, thymus, and lymph nodes) characterized by abnormal and compactly arranged plasmocytoid cells, and glomerulonephritis leading to glomerulosclerosis similar to multiple myeloma.

Microinjection into fertilized eggs of a C57BL/6J mouse of a $H-2L^d$-driven hIL-6 cDNA caused IL-6-dependent muscle wasting in mice, characterized in part by a significantly lower gastrocnemius muscle weight in transgenic mice as compared to weight-matched controls, a difference that was ameliorated by treatment with an IL-6 antagonist (see, Tsujinaka et al. (1996) Interleukin 6 Receptor Antibody Inhibits Muscle Atrophy and Modulates Proteolytic Systems in Interleukin 6 Transgenic Mice, J. Clin. Invest. 97(1):244-249). At 12 weeks these mice displayed serum hIL-6 levels of more than 600,000 pg/mL. The transgenic mice also had livers that weighed about 1,242 mg, as compared to control livers that were about 862 mg. Transgenic mice treated with IL-6 antagonist had livers that weighed about 888 mg. Muscle cathepsins B and B+L were significantly higher (20-fold and 6.2-fold) in transgenic mice than in controls, a phenomenon that was eliminated in transgenic mice treated with an IL-6 antagonist. cathepsin B and L mRNAs were estimated to be about 277% and 257%, respectively, as compared with wild-type mice; the difference was significantly reduced with IL-6 antagonist treatment.

Mice comprising a hIL-6 minigene driven by a mouse MHC class I H-2Ld promoter and a hIL-6R minigene driven by a chicken β-actin promoter, and a gp130 gene, exhibited pathologies typical of hIL-6 transgenic mice (e.g., hepergammaglobulinemia, splenomegaly, mesangial proliferative glomerulonephritis, lung lymphoid infiltration) as well as ventricular hypertrophy (Hirota et al. (1995) Continuous activation of gp130, a signal-transducing receptor component for interleukin 6-related cytokines, causes myocardial hypertrophy in mice, Proc. Natl Acad. Sci. USA 92:4862-4866). The ventricular hypertrophy is believed to be mediated by a continuous activation of gp130 (Id.). The role of IL-6 is reportedly to help strengthen the cytokine receptor complex and induce dimerization of gp130, which is the signal transducing component responsible for transducing the IL-6 signal (Paonessa et al. (1995) Two distinct and independent sites on IL-6 trigger gp130 dimer formation and signalling, EMBO J. 14(9):1942-1951). The activated complex is believed to be a hexamer composed of two IL-6, each IL-6 bound to one IL-6Rα and two gp130 (each IL-6 contains two independent gp130-binding sites) exhibiting a 2:2:2 stoichiometry, wherein the dimerization of gp130 causes activation of JAK-Tyk tyrosine kinases, phosphorylation of gp130 and STAT family transcription factors and other intracellular substrates (Id.; Stahl, N. (1994) Association and Activation of Jak-Tyk Kinases by CNTF-LIF-OSM-IL-6β Receptor Components, Science 263:92-95), consistent with a general model of cytokine receptor complex formation (see, Stahl, N. and Yancopoulos, G. (1993) The Alphas, Betas, and Kinases of Cytokine Receptor Complexes, Cell 74:587-590; Davis et al. (1993) LIFRβ and gp130 as Heterodimerizing Signal Transducers of the Tripartite CNTF Receptor, Science 260:1805-1808; Murakami et al. (1993) IL-6-Induced Homodimerization of gp130 and Associated Activation of a Tyrosine Kinase, Science 2601808-1810).

Mice transgenic for human sIL-6R driven by a rat PEP carboxykinase promoter and human IL-6 driven by a mouse metallothionein-1 promoter are reportedly markedly smaller that mice transgenic for human IL-6 alone or human sIL-6R alone (Peters et al. (1997) Extramedullary Expansion of Hematopoietic Progenitor Cells in Interleukin (IL-)-6-sIL-6R Double Transgenic Mice, J. Exp. Med. 185(4):755-766), reflected in reduced body fat and reduced weight (20-25 g vs. 40 g). Double transgenic mice reportedly also exhibit spleen (5-fold) and liver (2-fold) enlargement as compared with reportedly normal organ weights for single transgenic mice, apparently due to extramedullary proliferation of hematopoeitic cells of spleena and liver but not bone marrow, as well as elevated megakaryocytes in spleen and plasmacellular infiltrates in all parenchymal organs (Id.). Double transgenics also exhibit livers with an increase of about 200- to about 300-fold in granulocytes, macrophages, progenitor cells, and B cells as compared with single transgenics; in contrast, IL-6 single transgenic mice exhibited lesser increases in macrophages (15-fold) and B cells (45-fold) (Id.). The extraordinary findings are presumably due to stimulation of growth and differentiation of hematopoietic progenitor cells by activating gp130 signal transduction (Id.).

Further, double transgenic (mouse metallothionine promoter-driven hIL-6/rat PEP carboxykinase promoter-driven hIL-6R) mice exhibit a hepatocellular hyperplasia that is reportedly identical to human nodular regenerative hyperplasia with sustained hepatocyte proliferation that strongly suggests that IL-6 is responsible for both hepatocyte proliferation and pathogenic hepatocellular transformation (Maione et al. (1998) Coexpression of IL-6 and soluble IL-6R causes nodular regenerative hyperplasia and adenomas of the liver, EMBO J. 17(19):5588-5597). Because hepatocellular hyperplasia is reportedly not observed in single transgenic hIL-6 mice and hIL-6 can bind mIL-6R, the finding may appear paradoxical until it is considered that the double transgenic may result in higher levels of hIL-6 complexed to soluble IL-6R (here, soluble hIL-6R), which complex is a more potent inhibitor that IL-6 alone (Id.).

In contrast to mice that are transgenic for human IL-6, humanized IL-6 mice that comprise a replacement at an endogenous mouse IL-6 locus, which retain mouse regulatory elements but comprise a humanization of IL-6-encoding sequence, do not exhibit the severe pathologies of prior art mice. Genetically modified mice that were heterozygous or homozygous for hIL-6 were grossly normal.

Figure 4:
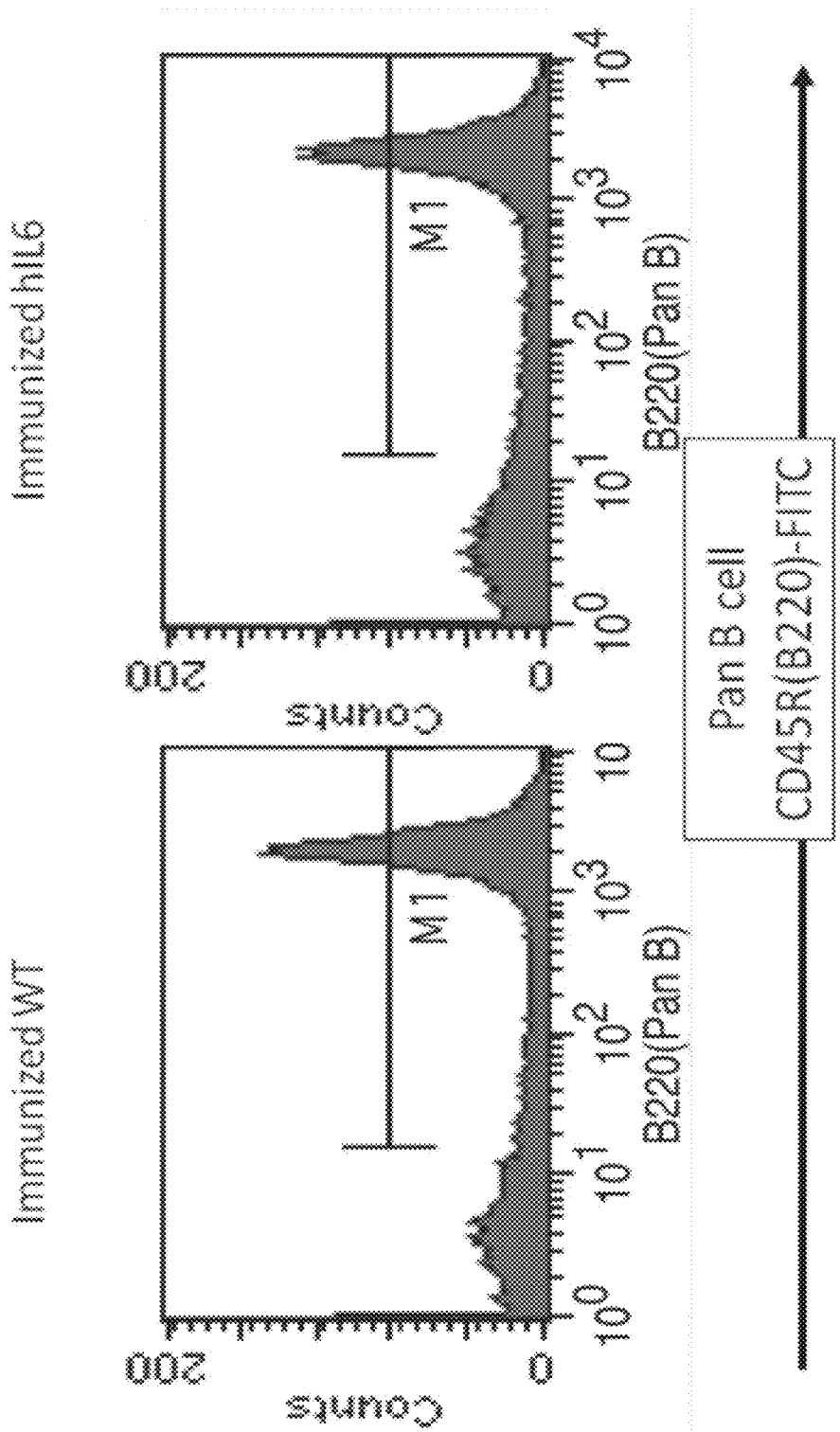
FIG. 4 shows FACS analysis for splenic B cells of wild-type (A) and humanized (B) IL-6 mice; pan B cell marker.

Mice with a humanized IL-6 gene (MAID 760) as described in the Examples were immunophenotyped and found to have normal B cell numbers in FACS analyses (lymphocyte-gated) of spleen B cells using a pan B cell marker (CD445R(B220)) (FIG. 4). For spleen, wild-type mice exhibited 63% B cells; hIL-6 heterozygote mice exhibited 63% B cells; and mice homozygous for hIL-6 at the endogeous mouse locus exhibited 63% B cells. B cell numbers for homozygous hIL-6 mice immunized with TNP-KLH were also normal (65% for wild-type, and 61% for hIL-6 homozygotes).

Figure 5:
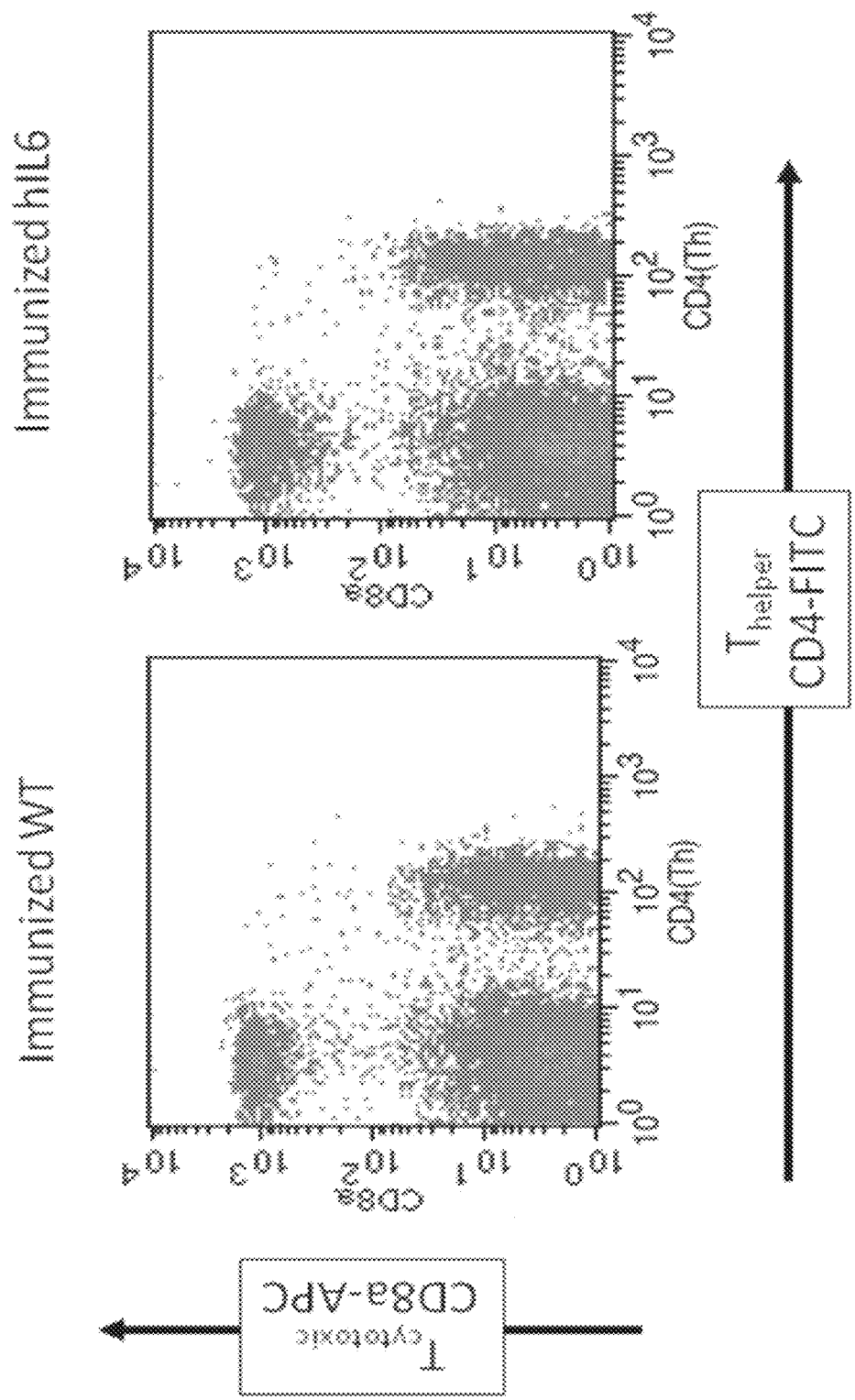
FIG. 5 shows FACS analysis for splenic T cells of wild-type (A) and humanized (B) IL-6 mice; T helper cells and cytotoxic T cells.

Splenic T cells were also about the same as wild-type (FIG. 5). Percentages of splenic T cells for Thelper/Tcytoxic were, for wild-type 20%/40% (ratio of 1.4:1); for hIL-6 heterozygotes 23%/14% (ratio of 1.6:1); for hIL-6 homozygotes 21%/15% (ratio of 1.4:1) (markers were CD8a-APC; CD4-FITC). Homozygous hIL-6 mice immunized with TNP-KLH exhibited similar splenic T cell numbers to wild-type mice, i.e., Thelper/Tcytotoxic were 22%/20% (ratio of 1.1:1) as compared with 21%/19% for wild-type (also a ratio of 1.1:1).

Figure 7:
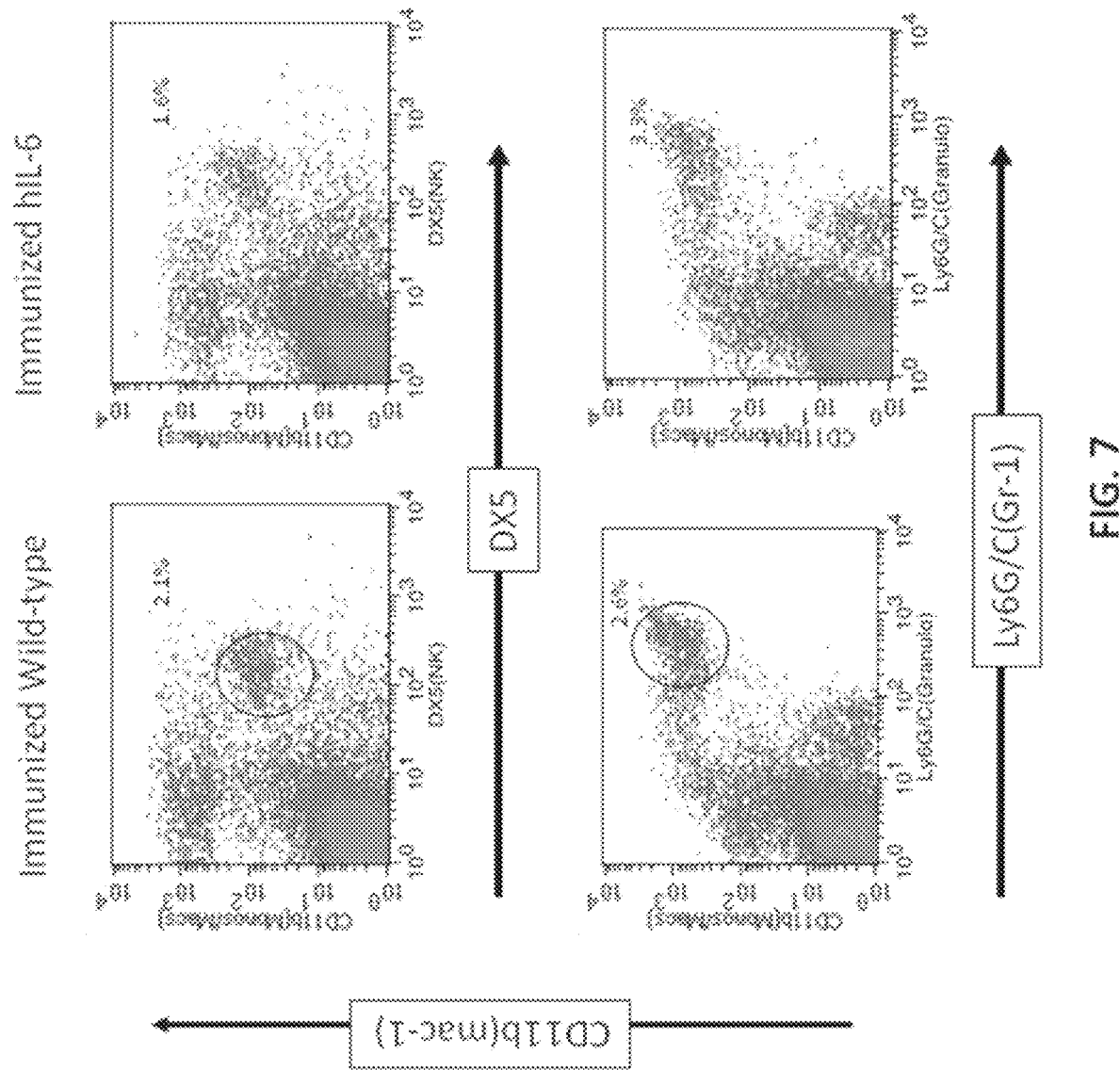
FIG. 7 shows FACS analysis for splenic cells of wild-type (A, C) and humanized (B, D) IL-6 mice; NK cells (A-B) and granulocytes (Ly6G$^{hi+}$/CD11b$^{hi+}$) (C-D).

Humanized IL-6 mice also exhibited about normal levels of splenic NK cells on FACS analysis (CD11b and DX5) (FIG. 7). hIL-6 heterozygotes exhibited 2.2% NK cells, and hIL-6 homozygotes exhibited 1.8% NK cells, whereas wild-type mice exhibited 2.4% NK cells. Following immunization with TNP-KLH, homozygotes exhibited 1.6% splenic NK cells, whereas wild-type mice exhibited 2.1% splenic NK cells.

Figure 6:
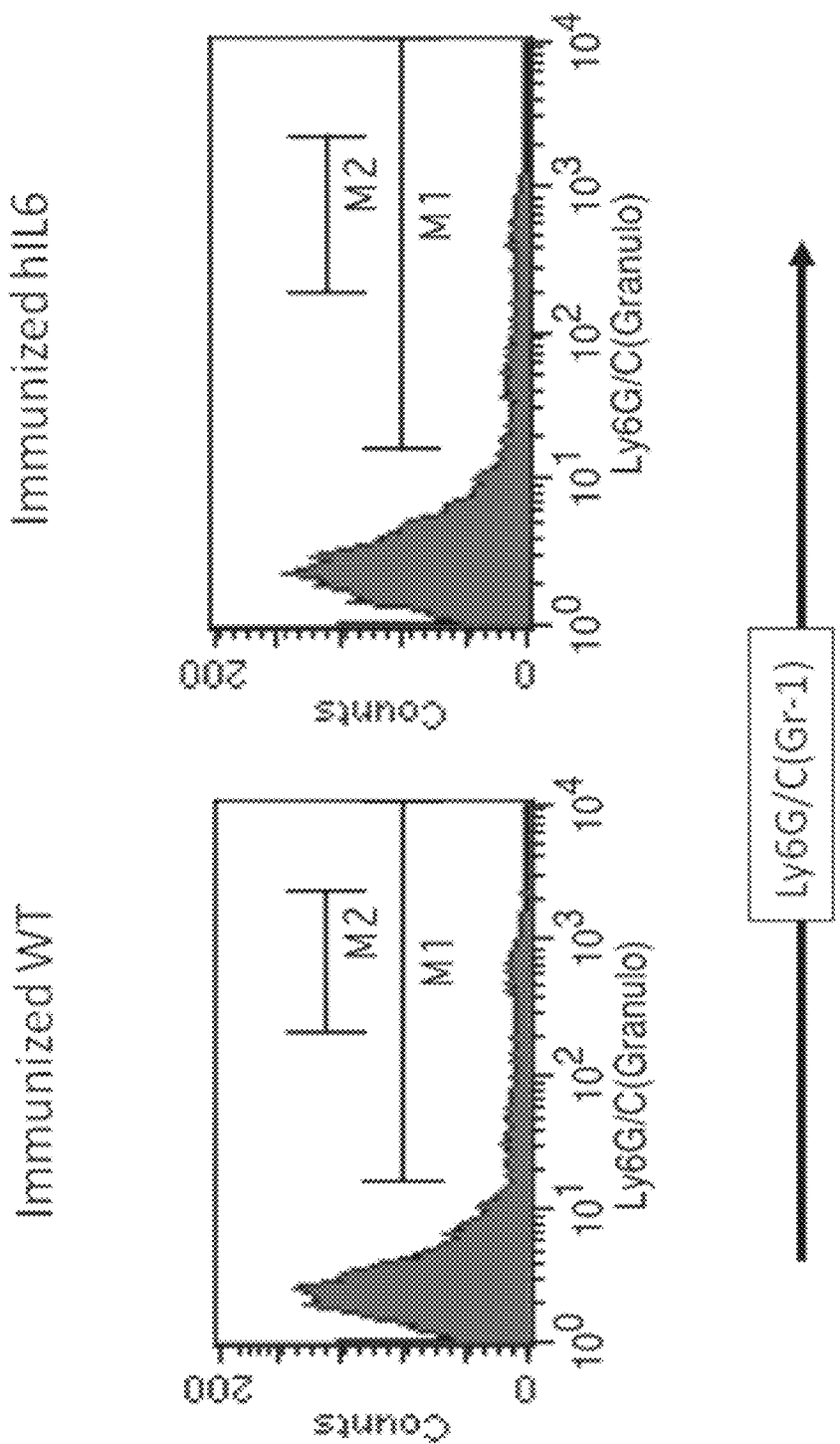
FIG. 6 shows FACS analysis for splenic cells of wild-type (A) and humanized (B) IL-6 mice; Ly6G/C(Gr1).

Humanized IL-6 mice also exhibited normal levels of splenic Ly6G/C(Gr1) cells (FIG. 6). hIL-6 heterozygotes exhibited 7.0% Gr1$^+$ cells (1.3% Gr1$^{hi}$); homozygotes exhibited 6.8% Gr1$^+$ cells (0.9% Gr1$^{hi}$), whereas wild-type mice exhibited 8.0% Gr1$^{hi}$ cells (1.8% Gr1$^{hi}$). Immunized IL-6 homozygotes (immunized with TNP-KLH) exhibited 11% Gr1+ cells (4.0% Gr1$^{hi}$), whereas wild-type mice exhibited 10% Gr1$^+$ cells (3.0% Gr1$^{hi}$).

Figure 8:
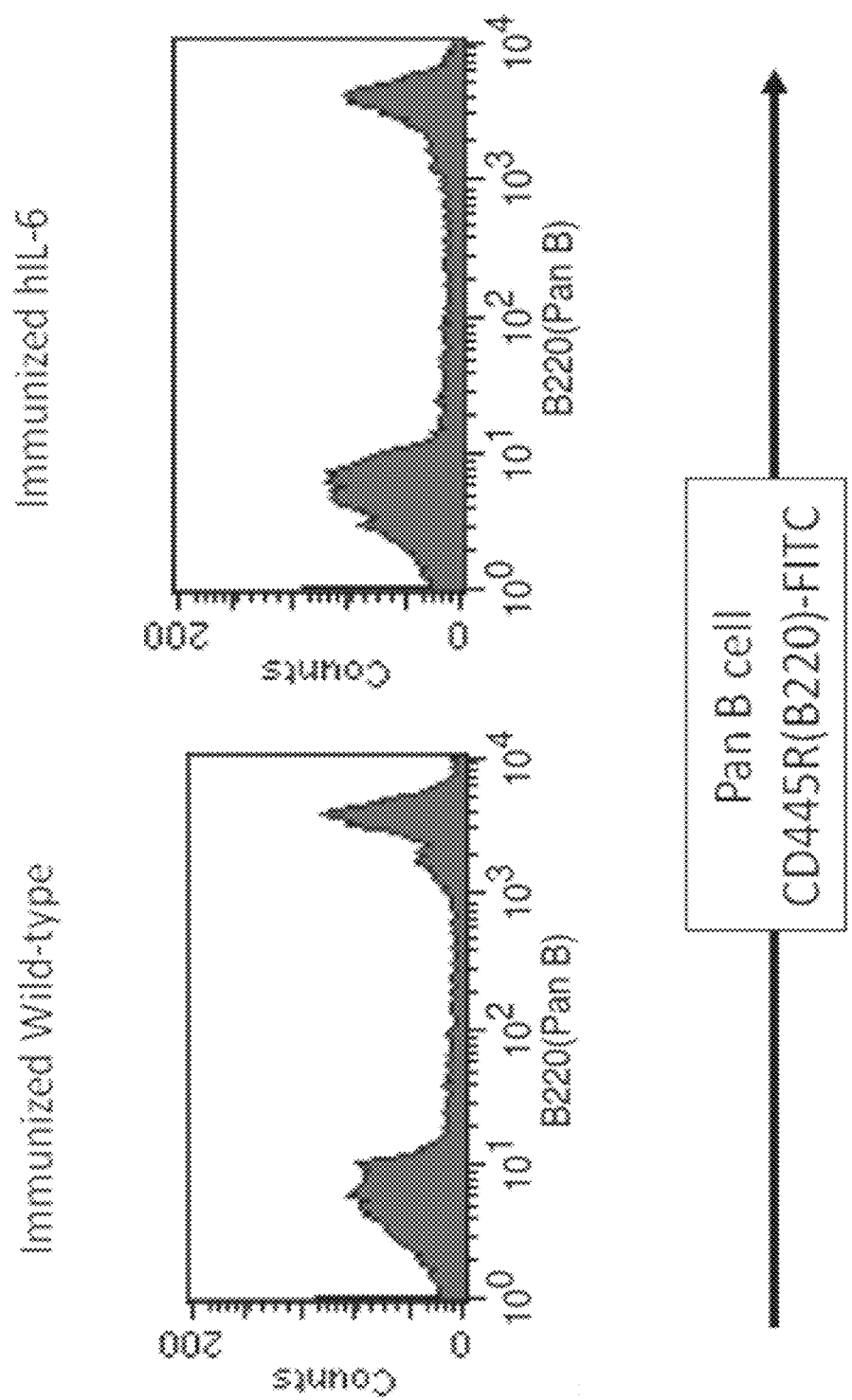
FIG. 8 shows FACS analysis for blood B cells of wild-type (A) and humanized (B) IL-6 mice; pan B cell marker.
Figure 9:
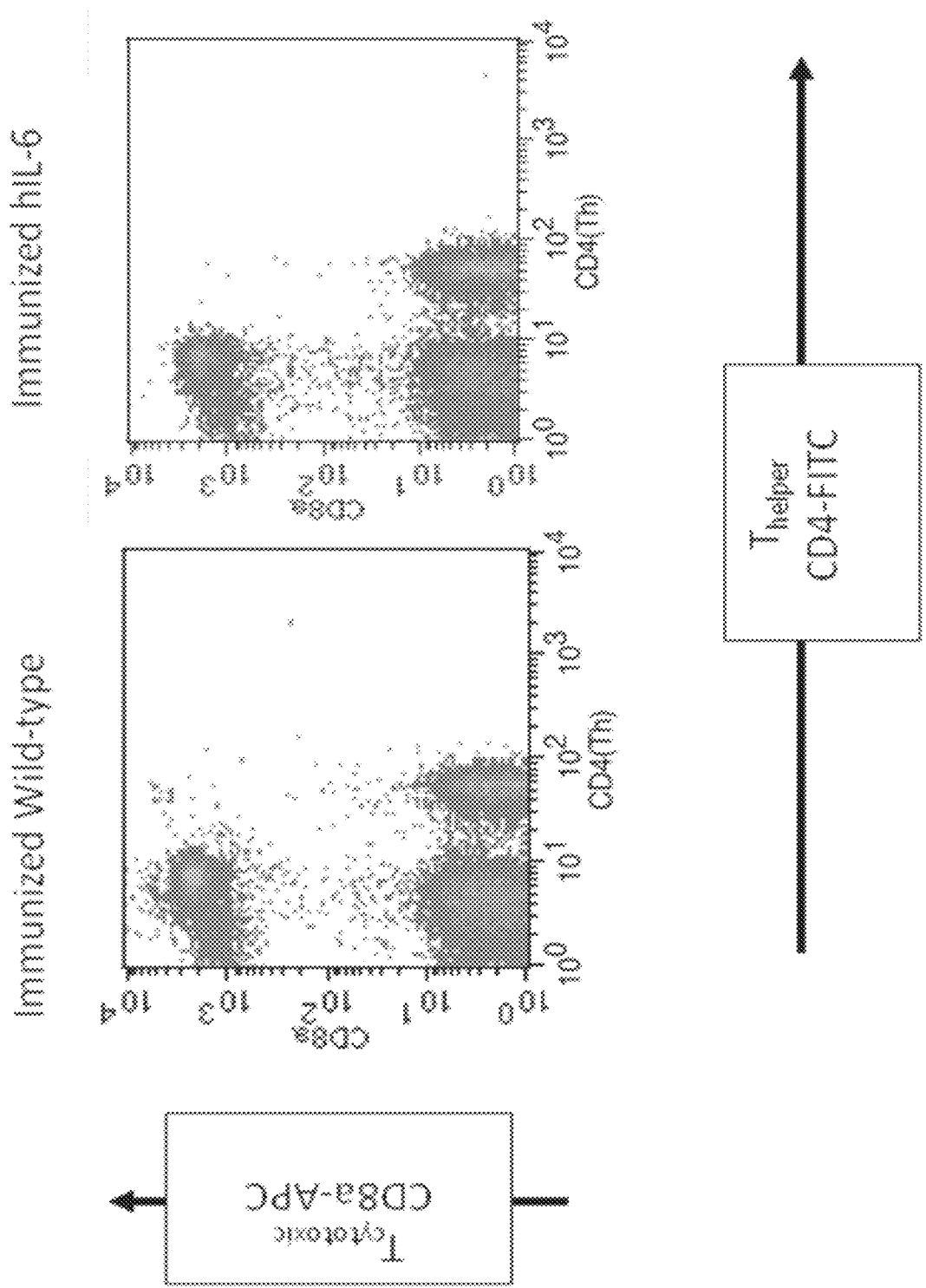
FIG. 9 shows FACS analysis for blood T cells of wild-type (A) and humanized (B) IL-6 mice; T helper cells and cytotoxic T cells.

Humanized IL-6 mice also exhibited normal blood B and T cell numbers in FACS analysis (FIG. 8 and FIG. 9). FACs with a pan B cell marker (CD445R(B220)) revealed that homozygous hIL-6 mice exhibited 52% B cell as compared with wild-type 53%; heterozygotes exhibited 38% (an average of two different stainings of 29% and 47%). Homozygous hIL-6 mice immunized with TNP-KLH gave similar B cell numbers (43%, as compared with 45% for wild-type mice).

Humanized IL-6 mice exhibited normal blood T cell numbers in FACS analysis as measured by CD8a and CD4 staining. Heterozygous hIL-6 mice exhibited Thelper/Tcytotoxic numbers of 39%/26% (ratio of 1.5:1); homozygous hIL-6 mice exhibited Th/Tc numbers of 24%/20% (ratio of 1.2:1), whereas wild-type mice exhibited Th/Tc numbers of 26%/20% (ratio of 1.3:1). Homozygous hIL-6 mice immunized with TNP-KLH had Th/Tc numbers of 29%/21% (ratio of 1.4:1), whereas wild-type immunized mice had Th/Tc numbers of 28%/23% (1.2:1).

Figure 10:
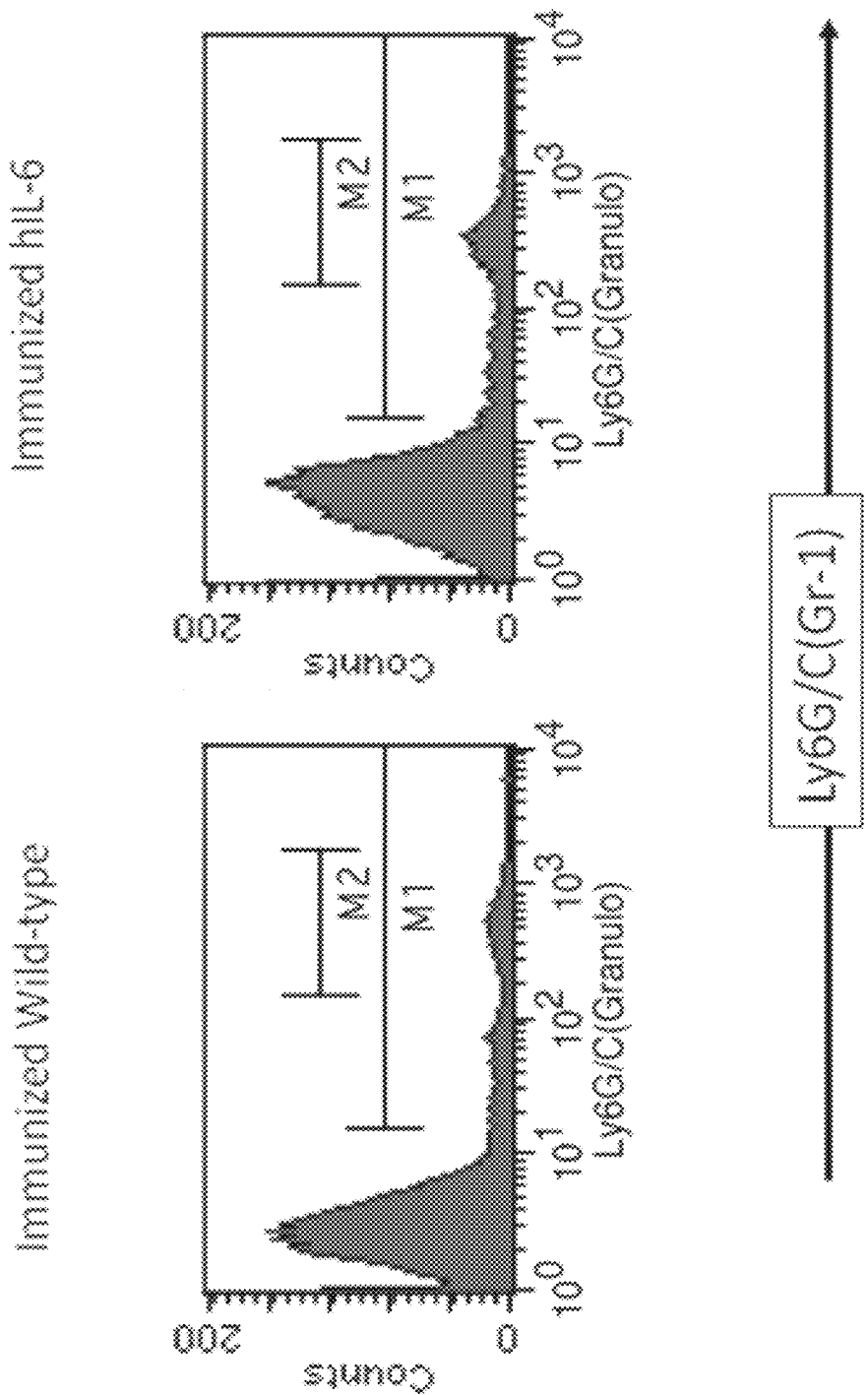
FIG. 10 shows FACS analysis for blood myeloid cells of wild-type (A) and humanized (B) IL-6 mice; Gr1$^+$ cells.
Figure 11:
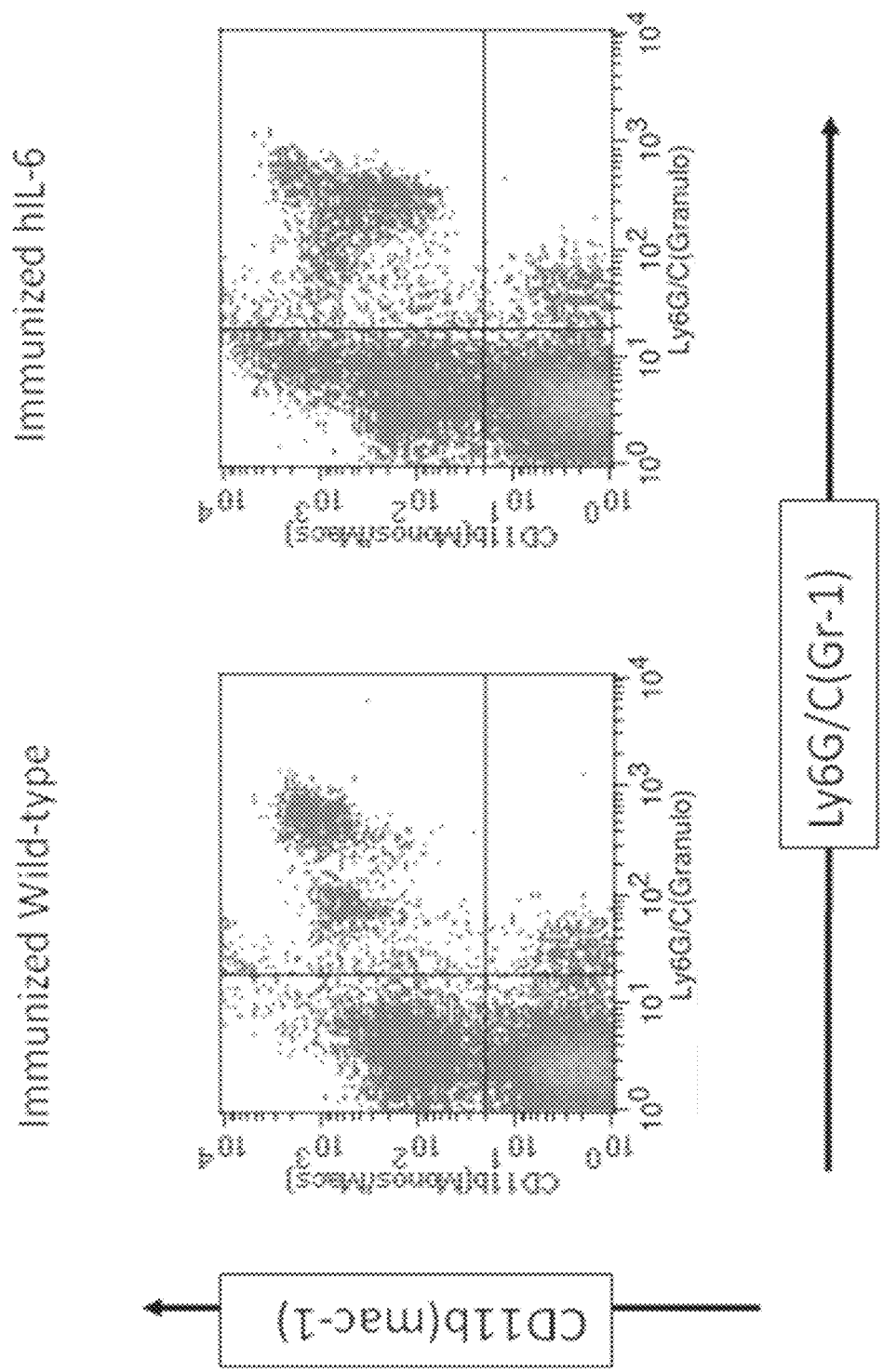
FIG. 11 shows FACS analysis for blood myeloid cells of wild-type (A) and humanized (B) IL-6 mice; CD11b vs. Ly6G/C(Gr1).
Figure 12:
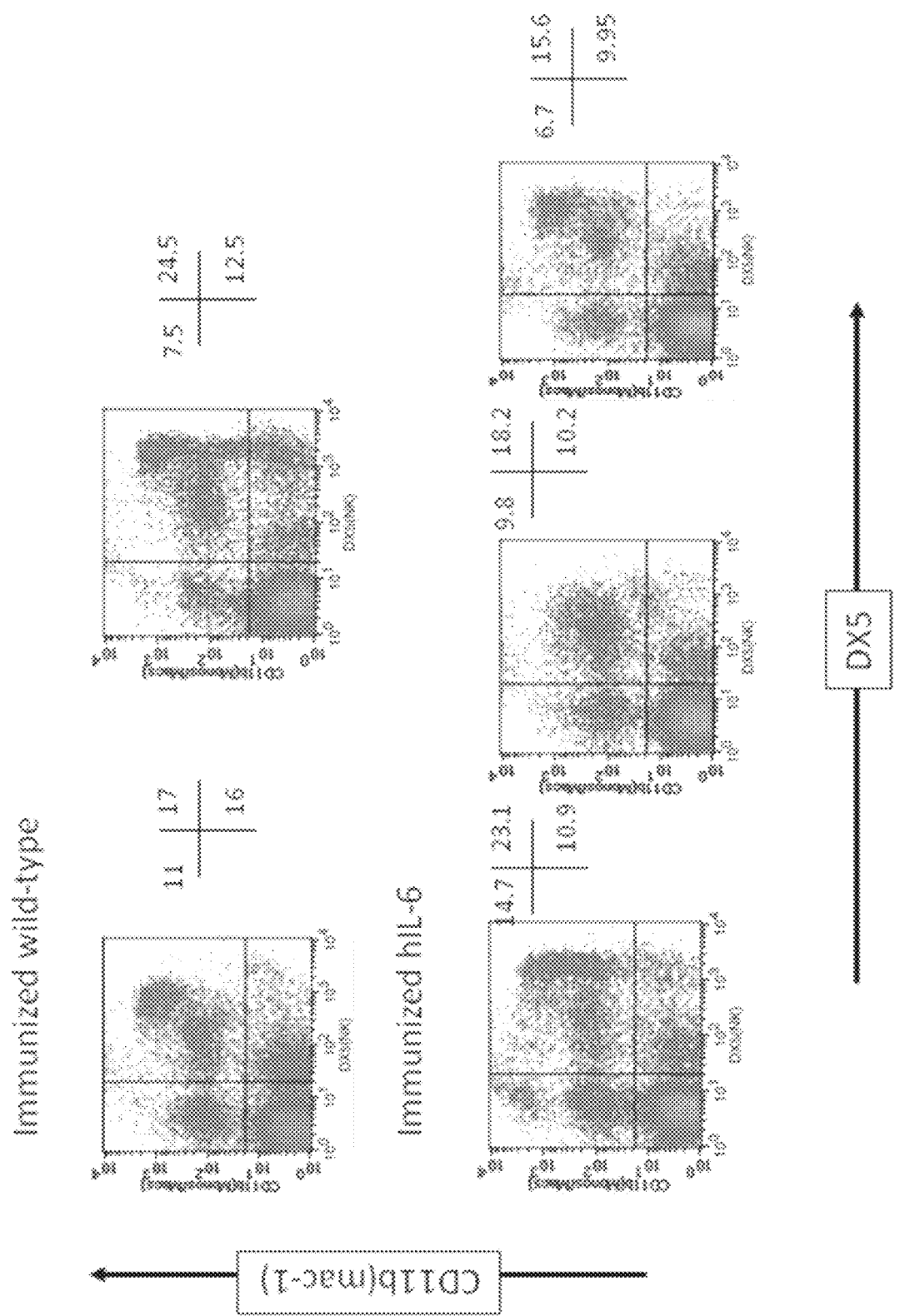
FIG. 12 shows FACS analysis for blood myeloid cells of wild-type (A-B) and humanized (C-D) IL-6 mice; DX5 vs CD11b cells.

Humanized IL-6 mice also exhibited myeloid cell numbers in blood that were similar to wild-type mice as measured by FACS analysis of naïve and immunized mouse blood stained with Ly6G/C(Gr1) and CD11b, as well as CD11b and DX5 (FIG. 10, FIG. 11, and FIG. 12). Heterozygous hIL-6 mice exhibited % Gr+ cells of 10.8%, homozygotes 6.9%, whereas wild-type mice exhibited 9.7%. Immunized hIL-6 homozygotes exhibited M1(Ly6G/C(Gr) of $10^1$-$10^4$)/M2(Ly6G/C(Gr) staining of about $10^2$-10) numbers of 43%/34%, whereas wild-type mice had numbers of 45%/38%. FACS plots of CD11b (vertical axis) vs. Ly6G/C (horizontal axis) for immunized homozygous hIL-6 mice showed cell percentage in quadrants (upper left/upper right/lower right) of 16%/8%/3%, which were identical to immunized wild-type quadrant numbers.

Homozygous TNP-KLH-immunized humanized IL-6 mice exhibited CD11b vs. DX5(NK) staining FACS plots that were similar to immunized wild-type mice. Quadrant analysis blood FACS plots (CD11b vertical axis, DX5(NK) horizontal axis) revealed upper left/upper right/lower right numbers of 9.5%/17%/10% for hIL-6 homozygotes and 6.5%/17.3%/14% for wild-type mice.

Humanized IL-6 mice exhibited an isotype response that was essentially the same as observed in wild-type mice. Early and final IgG1, IgG2a, IgG2b, IgG3, IgA, IgE, and IgM levels were about the same as observed in wild-type mice. In one experiment, final IgM was slightly higher in humanized mice; final IgG3 was also elevated in humanized mice.

Figure 13:
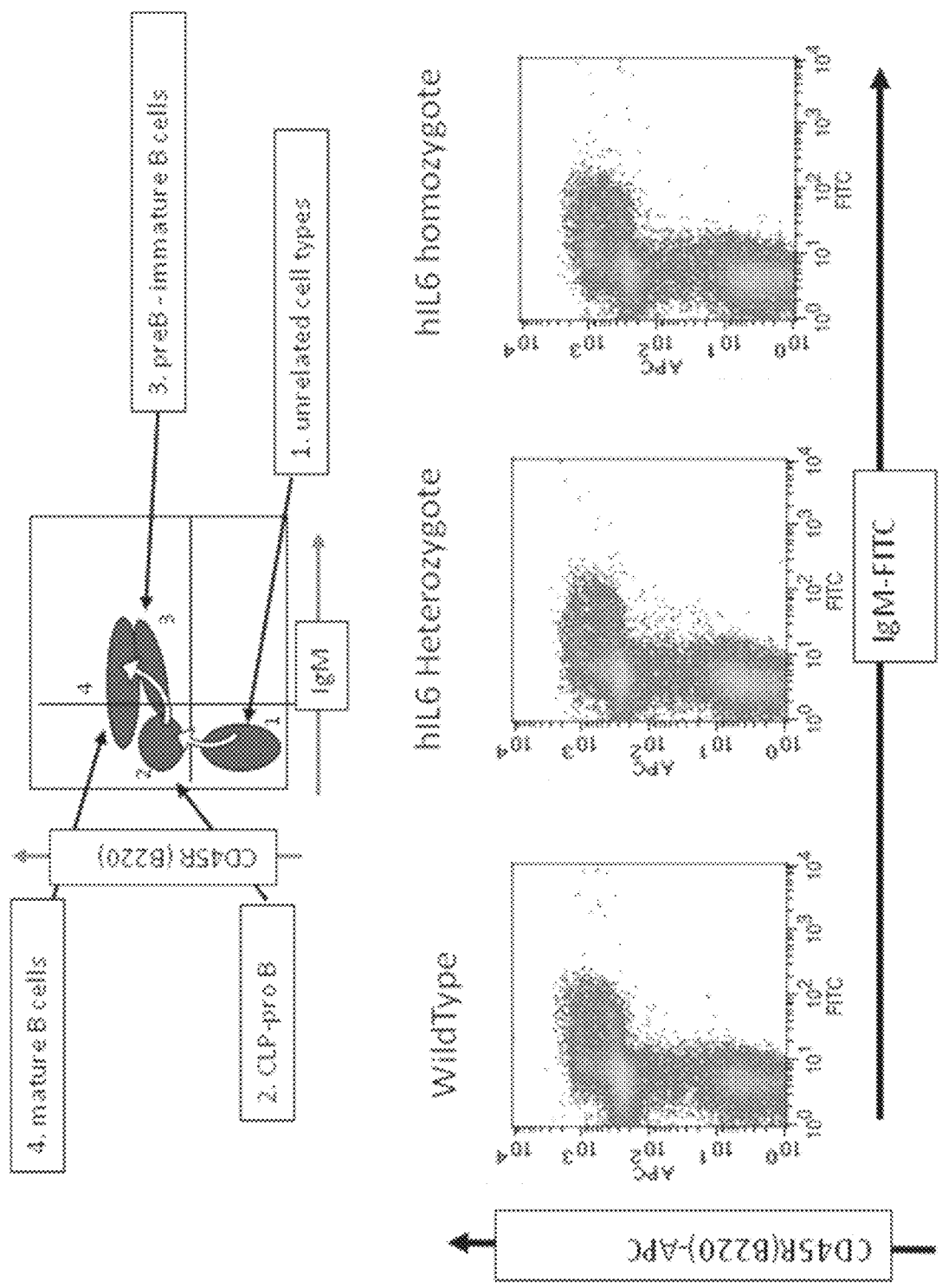
FIG. 13 shows FACS analysis of bone marrow IgM/CD24/B220 for wild-type and humanized IL-6 mice. A: normal progression in bone marrow. B-D: FACS analysis for wild-type (B), hIL-6 heterozygotes (C), and hIL-6 homozygotes (D) (IgM staining).
Figure 14:
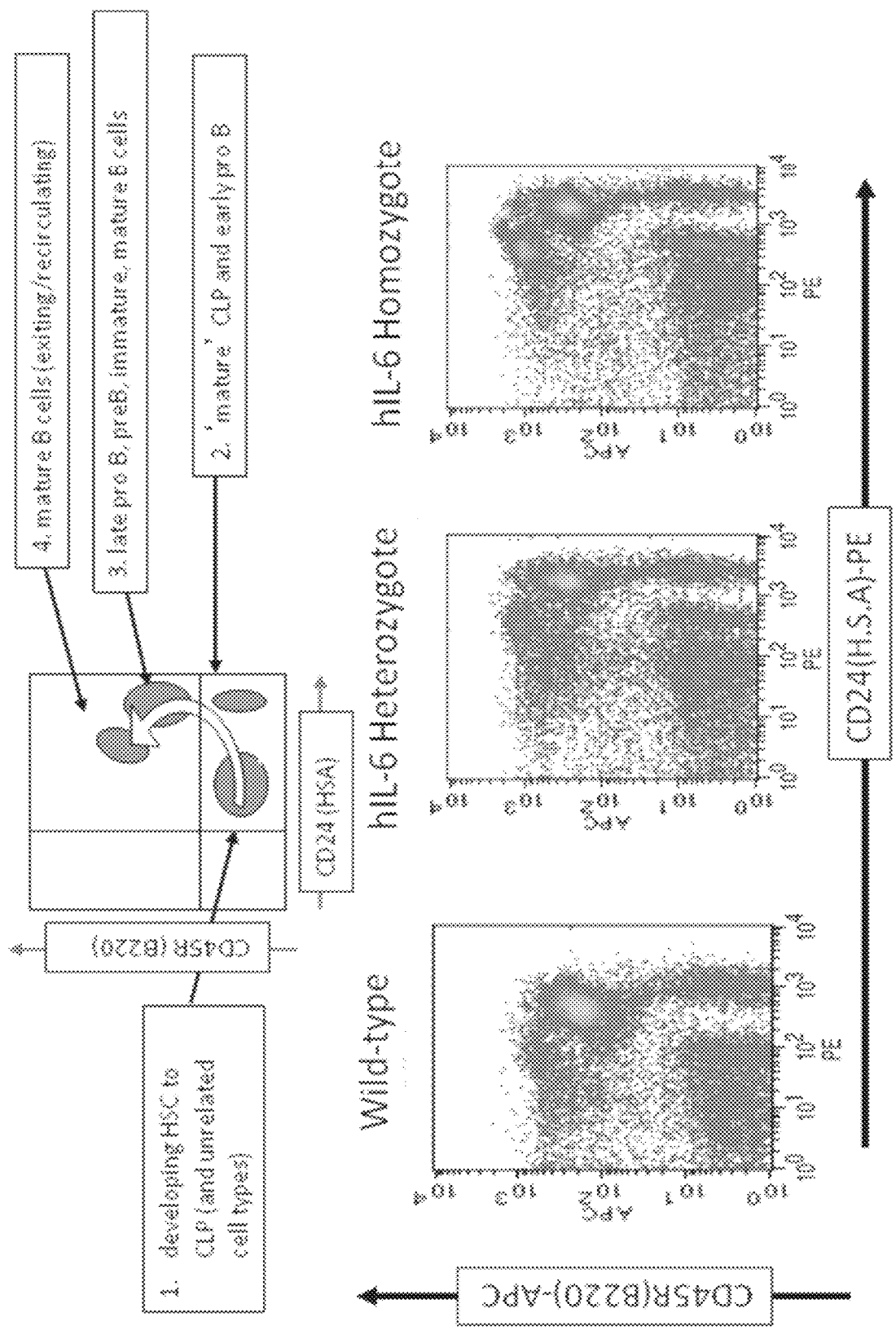
FIG. 14 shows FACS analysis of bone marrow IgM/CD24/B220 for wild-type and humanized IL-6 mice. A: normal progression in bone marrow. B-D: FACS analysis for wild-type (B), hIL-6 heterozygotes (C), and hIL-6 homozygotes (D) (CD24 staining).
Figure 15:
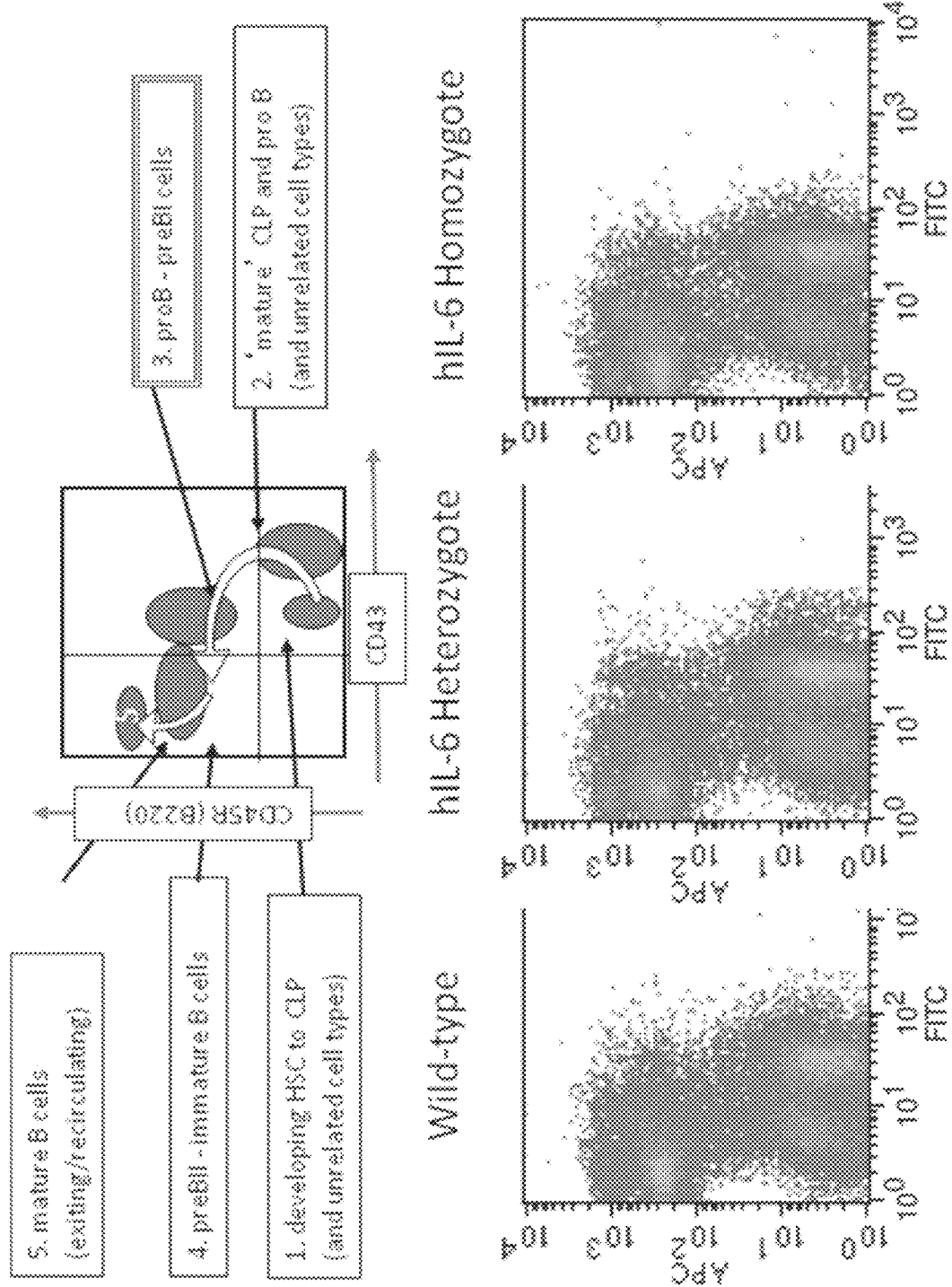
FIG. 15 shows FACS analysis of bone marrow CD43 and B220 for wild-type and humanized IL-6 mice. A: normal progression in bone marrow. B-D: FACS analysis for wild-type (B), hIL-6 heterozygotes (C), and hIL-6 homozygotes (D) (CD43 staining).

B cell development in naïve hIL-6 mice was essentially indistinguishable from development in wild-type mice based on FACS analysis of bone marrow IgM/CD24/B220 staining (FIG. 13). Immunophenotyping of immune mice revealed that marker populations for various cell types in the B cell development progression were essentially normal in hIL-6 mice. Progression of cells from hematopoietic stem cells, common lymphoid progenitors, ProB cells, PreB cells, and immature and mature B cells is normal in hIL-6 mice (FIG. 14 and FIG. 15)

EXAMPLES

Example 1: Replacement of Endogenous Mouse IL-6 Gene with hIL-6 Gene

The 4.8-kb human IL-6 gene containing exons 1 through 5 of the human IL-6 gene replaced 6.8 kb of the murine IL-6 gene locus.

A targeting construct for replacing the mouse with the human IL-6 gene in a single targeting step was constructed using VELOCIGENE® genetic engineering technology (see, Valenzuela et al. (2003) High-throughput engineering of the mouse genome coupled with high-resolution expression analysis, Nature Biotech, 21(6):652-659). Mouse and human IL-6 DNA were obtained from bacterial artificial chromosome (BAC) RPCI-23 clone 368C3, and from BAC CTD clone 2369M23, respectively. Briefly, a NotI linearized targeting construct generated by gap repair cloning containing mouse IL-6 upstream and downstream homology arms flanking a 4.8 kb human IL-6 sequence extending from ATG in exon 1 to exon 5 with 16 nucleotides of 3' downstream sequence (genomic coordinates: NCBIh37.1: ch7:22,766,882 to 22,771,637) and a floxed neo selection cassette, was electroporated into F1H4 mouse embryonic stem (ES) cells (C57BL/6×129 F1 hybrid). Correctly targeted ES cells (MAID 790) were further electroporated with a transient Cre-expressing vector to remove the drug selection cassette. Targeted ES cell clones without drug cassette (MAID 1428) were introduced into an 8-cell stage mouse embryo by the VELOCIMOUSE® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) bearing the humanized IL-6 gene were identified by genotyping for loss of mouse allele and gain of human allele using a modification of allele assay (see, Valenzuela et al. (2003)).

Correctly targeted ES cell clones were identified by a loss-of-native-allele (LONA) assay (Valenzuela et al. 2003) in which the number of copies of the native, unmodified Il6 gene were determined by two TaqMan™ quantitative polymerase chain reactions (qPCRs) specific for sequences in the mouse Il6 gene that were targeted for deletion. The qPCR assays comprised the following primer-probe sets (written 5' to 3'): upstream forward primer, TTGCCGGTTT TCCCTTTTCT C (SEQ ID NO:1); upstream reverse primer, AGGGAAGGCC GTGGTTGTC (SEQ ID NO:2); upstream probe, FAM-CCAGCATCAG TCCCAAGAAG GCAACT-BHQ (SEQ ID NO:3); downstream forward primer, TCAGAGTGTG GGCGAACAAA G (SEQ ID NO:4); downstream reverse primer, GTGGCAAAAG CAGCCT-TAGC (SEQ ID NO:5); downstream probe, FAM-TCAT-TCCAGG CCCTTCTTAT TGCATCTG-BHQ (SEQ ID NO:6); in which FAM refers to the 5-carboxyfluorescein fluorescent probe and BHQ refers to the fluorescence quencher of the black hole quencher type (Biosearch Technologies). DNA purified from ES cell clones that that have taken up the targeting vector and incorporated in their genomes was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream Il6-specific qPCRs and two qPCRs for non-targeted reference genes were run for each DNA sample. The differences in the Ct values (ΔCt) between each Il16-specific qPCR and each reference gene qPCR were calculated, and then the difference between each ΔCt and the median ΔCt for all samples assayed was calculated to obtain ΔΔCt values for each sample. The copy number of the Il6 gene in each sample was calculated from the following formula: copy number=$2 \cdot 2^{-ct}$. A correctly targeted clone, having lost one of its native copies, will has an Il6 gene copy number equal to one. Confirmation that the human IL6 gene sequence replaced the deleted mouse Il6 gene sequence in the humanized allele was confirmed by a TaqMan™ qPCR assay that comprises the following primer-probe sets (written 5' to 3'): the human forward primer, CCCCACTCCACTGGAATTTG (SEQ ID NO:7); the human reverse primer, GTTCAACCACAGCCAGGAAAG (SEQ ID NO:8); and the human probe, FAM-AGCTA-CAACTCATTGGCATCCTGGCAA-BHQ (SEQ ID NO:9).

The same LONA assay was used to assay DNA purified from tail biopsies for mice derived from the targeted ES cells to determine their Il6 genotypes and confirm that the humanized Il6 allele had transmitted through the germline. Two pups heterozygous for the replacement are bred to generate a mouse that is homozygous for the replacement of the endogenous mouse IL-6 gene by the human IL-6 gene. Pups that are homozygous for the replacement are used for phenotyping.

The upstream junction of the murine locus and the sequence containing the hIL-6 gene is designed to be within 5'-AATTAGAGAG TTGACTCCTA ATAAATATGA GACTGGGGAT GTCTGTAGCT CATTCTGCTC TGGAGCCCAC CAAGAACGAT AGTCAATTCC AGAAACCGCT ATGAACTCCT TCTCCACAAG TAAGTGCAGG AAATCCTTAG CCCTGGAACT GCCAGCGGCG GTCGAGCCCT GTGTGAGGGA GGGGTGTGTG GCCCAGG (SEQ ID NO:10), wherein the final mouse nucleotide prior to the first nucleotide of the human gene is the "T" in CCGCT, and the first nucleotide of the human sequence is the first "A" in ATGAA. The downstream junction of the sequence containing the hIL-6 gene and the murine locus is designed to be within 5'-TTT-TAAAGAA ATATTTATAT TGTATTTATA TAATGTATAA ATGGTTTTTA TACCAATAAA TGGCATTTTA AAAAATTCAG CAACTTTGAG TGTGTCACGC TCCCGGGCTC GATAACTATA ACGGTCCTAA GGTAGCGACT CGAGATAACT T-3' (SEQ ID NO:11), wherein the final nucleotide of the human sequence is with the final "G" in TCACG and the first nucleotide of the mouse sequence is the first "C" in CTCCC; the downstream junction region also contained a loxP site at the 3' end (the beginning of which is shown) for removal of a floxed ubiquitin promoter-driven neo cassette. The junction of the neo cassette with the mouse IL-6 locus is designed to be within 5'-TATACGAAGT TATCCTAGGT TGGAGCTCCT AAGTTACATC CAAACATCCT CCCCCAAATC AATAATTAAG CACTTTTTAT GACATGTAAA GTTAAATAAG AAGTGAAAGC TGCAGATGGT GAGT-GAGA (SEQ ID NO:12), where the final "C" of AGCTC is the final nucleotide of the neo cassette; the first nucleotide of the mouse genome following the cassette is the initial "C" of CTAAG.

Example 2: Immunophenotyping of Naïve and Immunized hIL-6 Mice: B Cells

Mice homozygous for the hIL-6 gene replacement were analyzed for B cells (DC445R(B220). Lymphocyte-gated fractions from spleen cell preparations of naïve and immunized (TNP-KLH) hIL-6 mice were stained and immunophenotyped using flow cytometry. FACS analysis showed that the percentage of B cells of the spleen cell preparation as measured by CD45R(B220)-FITC staining were about the same (63% of cells) for preparations from naïve wild-type, hIL-6 heterozygotes, and hIL-6 homozygotes. For immunized mice, B cells accounted for about 65% of total cells of the spleen cell preparation in wild-type mice, and about 61% of total cells in hIL-6 homozygotes. Spleens of hIL-6 mice (both naïve and immunized) contain a population of B cells that is about the same size as the splenic B cell population in wild-type mice.

Bone marrow of wild-type, hIL-6 heterozygotes, and hIL-6 homozygotes was stained with B cell markers (CD45R(B220)-APC, CD24(HSA)-PE, or CD43 conjugated to a dye and/or IgM (IgM-FITC). B cell development in bone marrow of normal mice will be reflected in surface markers as cells progress from stem cells to early pro-B cells to late pro-B cells, to large pre-B cells to small pre-B cells to immature B cells and finally, to mature B cells. Common lymphocyte progenitor pro-B cells will express CD45R, and in later stages will express IgM as immature and later as mature B cells. Thus, CD45R-stained and anti-IgM-stained B cells should reveal a pattern characteristic of B cell development. Bone marrow of hIL-6 heterozygotes and homozygotes displayed a pattern of CD45R(B220)-APC and anti-IgM-FITC staining that was essentially indistinguishable from wild-type bone marrow, showing populations of B cells that stained positive for CD45R(B220) and IgM, or CD45R(B220) alone. B cell sub-populations in bone marrow of hIL-6 mice revealed by FACS staining were similar to those in wild-type mice (Table 1; see also, FIG. 13).

TABLE 1

B Cells in Bone Marrow of Naive Mice

| | Wild-type Mouse (%) | hIL-6 Mouse Heterozygote (%) | hIL-6 Mouse Homozygote (%) |
|---|---|---|---|
| CLP-ProB | 40 | 29 | 32 |
| PreB-ImmatureB | 12.3 | 19.3 | 15.3 |
| Mature B | 6.4 | 6.5 | 6.7 |

Staining for CD24 (see FIG. 14) revealed the (normal) pattern shown in Table 2, indicating normal development in bone marrow.

TABLE 2

B Cells in Bone Marrow of Naive Mice

| | Wild-type Mouse (%) | hIL-6 Mouse Heterozygote (%) | hIL-6 Mouse Homozygote (%) |
|---|---|---|---|
| Developing HSC-CLP | 46.6 | 46 | 43 |
| Mature CLP/early ProB | 10.2 | 9.0 | 10.1 |
| Late ProB, PreB, Immature B | 7.2 | 11.6 | 10.7 |
| Mature B | 14.1 | 14.9 | 17 |

Staining for CD43 (see FIG. 15) revealed the (normal) pattern shown in Table 3, indicating normal development in bone marrow.

TABLE 3

B Cells in Bone Marrow of Naive Mice

| | Wild-type Mouse (%) | hIL-6 Mouse Heterozygote (%) | hIL-6 Mouse Homozygote (%) |
|---|---|---|---|
| PreBII-Immature B cells | 28.4 | 21.4 | 21.2 |
| Mature B cells | 8.1 | 11.5 | 8.0 |
| ProB-PreBI | 3.4 | 4.3 | 4.7 |

Thus, immunophenotyping of naïve hIL-6 mice revealed that B cell development in such mice is essentially normal.

Example 3: Replacement of Endogenous Mouse IL-6Rα Ectodomain Gene Sequence with hIL-6Rα Ectodomain Gene Sequence The 45 kb human IL-6Rα gene containing exons 1 through 8 of the human IL-6Rα gene replaced 35.4 kb of the murine IL-6Rα gene locus. Mouse exons 9 and 10 were retained; only exons 1-8 were humanized. In total, 35,384 nt of mouse sequence was replaced by 45,047 nt of human sequence.

A targeting construct for replacing the mouse with the human IL-6Rα gene in a single targeting step was constructed using VELOCIGENE® genetic engineering technology (see, Valenzuela et al. (2003) High-throughput engineering of the mouse genome coupled with high-resolution expression analysis, Nature Biotech, 21(6):652-659). Mouse and human IL-6Rα DNA were obtained from bacterial artificial chromosome (BAC) RPCI-23 clone 125J8, and from BAC CTD clone 2192J23, respectively. Briefly, a NotI linearized targeting construct generated by gap repair cloning containing mouse IL-6Rα upstream and downstream homology arms flanking a 45 kb human IL-6Rα sequence extending from ATG in exon 1 to exon 8 with 69 nucleotides of 3' downstream sequence and a floxed neo selection cassette, was electroporated into F1H4 mouse embryonic stem (ES) cells (C57BL/6×129 F1 hybrid). Correctly targeted ES cells (MAID 794) were further electroporated with a transient Cre-expressing vector to remove the drug selection cassette. Targeted ES cell clones without drug cassette (MAID 1442) were introduced into an 8-cell stage mouse embryo by the VELOCIMOUSE® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) bearing the humanized IL-6Rα gene were identified by genotyping for loss of mouse allele and gain of human allele using a modification of allele assay (see, Valenzuela et al. (2003)).

Correctly targeted ES cell clones were identified by a loss-of-native-allele (LONA) assay (Valenzuela et al. 2003) in which the number of copies of the native, unmodified Il6 gene were determined by two TaqMan™ quantitative polymerase chain reactions (qPCRs) specific for sequences in the mouse Il6 gene that were targeted for deletion. The qPCR assays comprised the following primer-probe sets (written 5' to 3'): upstream forward primer, GCCCTAGCAT GCAGAATGC (SEQ ID NO:13); upstream reverse primer, AAGAGGTCCC ACATCCTTTG C (SEQ ID NO:14); upstream probe, CCCACATCCA TCCCAATCCT GTGAG (SEQ ID NO:15); downstream forward primer, GAGCTTGCCC CCAGAAAGG (SEQ ID NO:16); downstream reverse primer, CGGCCACATC TCTGGAAGAC (SEQ ID NO:17); downstream probe, CATGCACTGC CCCAAGTCTG GTTTCAGT (SEQ ID NO:18). DNA purified from ES cell clones that that have taken up the targeting vector and incorporated in their genomes was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream IL-6Rα-specific qPCRs and two qPCRs for non-targeted reference genes were run for each DNA sample. The differences in the Ct values (ΔCt) between each IL-6Rα-specific qPCR and each reference gene qPCR were calculated, and then the difference between each ΔCt and the median ΔCt for all samples assayed was calculated to obtain ΔΔCt values for each sample. The copy number of the Il6 gene in each sample was calculated from the following formula: copy number=2·2−ΔΔCt. A correctly targeted clone, having lost one of its native copies, will have an IL-6Rα gene copy number equal to one. Confirmation that the human IL-6Rα gene sequence replaced the deleted mouse IL-6Rα gene sequence in the humanized allele was confirmed by a TaqMan™ qPCR assay that comprises the following primer-probe sets (written 5' to 3'): the human forward primer, GGAGAGGGCA GAGGCACTTA C (SEQ ID NO:19); the human reverse primer, GGCCAGAGCC CAAGAAAAG (SEQ ID NO:20); and the human probe, CCCGTTGACT GTAATCTGCC CCTGG (SEQ ID NO:21).

The same LONA assay was used to assay DNA purified from tail biopsies for mice derived from the targeted ES cells to determine their IL-6Rα genotypes and confirm that the humanized IL-6Rα allele had transmitted through the germline. Pups heterozygous for the replacement are bred to generate a mouse that is homozygous for the replacement of the endogenous mouse IL-6Rα gene by the human IL-6Rα (ectodomain) gene. Pups that are homozygous for the replacement are used for phenotyping.

The upstream junction of the murine locus and the sequence containing the hIL-6Rα gene is designed to be within 5'-CGAGGGCGAC TGCTCTCGCT GCCCCAGTCT GCCGGCCGCC CGGCCCCGGC TGCGGAGCCG CTCTGCCGCC CGCCGTCCCG CGTAGAAGGA AGCATGCTGG CCGTCGGCTG CGCGCTGCTG GCTGCCCTGC TGGCCGCGCC GGGAGCGGCG CTGGCCCCAA GGCGCTGCCC TGCGCAGGGT AAGGGCTTCG G (SEQ ID NO:22), wherein the final mouse nucleotide prior to the first nucleotide of the human gene is the "C" in GAAGC, and the first nucleotide of the human sequence is the first "A" in ATGCT. The downstream junction of the sequence containing the hIL-6 gene and the murine locus is designed to be within 5'-CAAGATTATT GGAGTCTGAA ATGGAATACC TGTTGAGGGA AATCTTTATT TTGGGAGCCC TTGATTTCAA TGCTTTTGAT TCCCTATCCC TGCAAGACCC GGGCTCGATA ACTATAACGG TCCTAAGGTA GCGACTCGAG ATAACTTC-3' (SEQ ID NO:23), wherein the final nucleotide of the human sequence is with the final "A" in CAAGA and the first nucleotide of the mouse sequence is the first "C" in CCCGG; the downstream junction region also contained a loxP site at the 3' end for removal of a floxed ubiquitin promoter-driven neo cassette. The first nucleotide of the loxp site is the first "A" in ATAAC. The junction of the neo cassette with the mouse IL-6Rα locus is designed to be within 5'-TATACGAAGT TATCCTAGGT TGGAGCTCTA CTCCATATGC TCACTTGCCG TTGTTTGCTA CGATACGGTG AGGCCCGTGC GAAGAGTGGC ACAGATCAGG AGGCTTATGT GGTCAGTCCA CAGTATGGC (SEQ ID NO:24), where the final "C" of AGCTC is the final nucleotide of the neo cassette; the first nucleotide of the mouse genome following the cassette is the initial "T" of TACTC.

We claim:

1. A rodent ES cell, comprising a replacement of a rodent nucleic acid encoding a rodent IL-6Rα ectodomain at an endogenous rodent IL-6Rα locus with a human nucleic acid encoding a human IL-6Rα ectodomain to form a humanized IL-6Rα gene, wherein the humanized IL-6Rα gene is under control of endogenous rodent regulatory elements at the endogenous rodent IL-6Rα locus, wherein the humanized IL-6Rα gene encodes a humanized IL-6Rα protein which comprises the human IL-6Rα ectodomain and rodent IL-6Rα transmembrane and cytoplasmic domains; and wherein the rodent ES cell is a mouse ES cell or a rat ES cell.

2. The rodent ES cell of claim 1, wherein the rodent ES cell is a mouse ES cell.

3. The rodent ES cell of claim 1, wherein the rodent ES cell is a rat ES cell.

4. The rodent ES cell of claim 1, wherein the rodent ES cell is heterozygous with respect to the replacement at the endogenous rodent IL-6Rα locus.

5. The rodent ES cell of claim 1, wherein the rodent ES cell is homozygous with respect to the replacement at the endogenous rodent IL-6Rα locus.

6. A rodent embryo comprising the rodent ES cell of claim 1.

7. A rodent ES cell, comprising
(i) a replacement of a rodent gene encoding IL-6 at an endogenous rodent IL-6 locus with a human gene encoding human IL-6, wherein the human gene encoding human IL-6 is under control of endogenous rodent regulatory elements at the endogenous rodent IL-6 locus; and
(ii) a replacement of a rodent nucleic acid encoding a rodent IL-6Rα ectodomain at an endogenous rodent IL-6Rα locus with a human nucleic acid encoding a human IL-6Rα ectodomain to form a humanized IL-6Rα gene, wherein the humanized IL-6Rα gene is under control of endogenous rodent regulatory elements at the endogenous rodent IL-6Rα locus, wherein the humanized IL-6Rα gene encodes a humanized IL-6Rα protein which comprises the human IL-6Rα ectodomain and rodent IL-6Rα transmembrane and cytoplasmic domains; and
wherein the rodent ES cell is a mouse ES cell or a rat ES cell.

8. The rodent ES cell of claim 7, wherein the rodent ES cell is a mouse ES cell.

9. The rodent ES cell of claim 7, wherein the rodent ES cell is a rat ES cell.

10. The rodent ES cell of claim 7, wherein the rodent ES cell is homozygous with respect to the replacement at the endogenous rodent IL-6 locus, and with respect to the replacement at the endogenous rodent IL-6Rα locus.

11. A rodent embryo comprising the rodent ES cell of claim 7.

* * * * *

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ttgccggttt tcccttttct c                                           21

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
agggaaggcc gtggttgtc                                              19

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
ccagcatcag tcccaagaag gcaact                                      26

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
tcagagtgtg ggcgaacaaa g                                           21
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
gtggcaaaag cagccttagc                                               20

<210> SEQ ID NO 6
<211> LENGTH: 28
<212> TYPE: DNA
<213> ORGANISM: Artificial Sequence
<220> FEATURE:
<223> OTHER INFORMATION: Synthetic

<400> SEQUENCE: 6
tcattccagg cccttcttat tgcatctg                                      28

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ccccactcca ctggaatttg                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gttcaaccac agccaggaaa g                                             21

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
agctacaact cattggcatc ctggcaa                                       27

<210> SEQ ID NO 10
<211> LENGTH: 197
<212> TYPE: DNA
<213> ORGANISM: Artificial Sequence
<220> FEATURE:
<223> OTHER INFORMATION: Synthetic

<400> SEQUENCE: 10
aattagagag ttgactccta ataaatatga gactggggat gtctgtagct cattctgctc   60
tggagcccac caagaacgat agtcaattcc agaaaccgct atgaactcct tctccacaag  120
taagtgcagg aaatccttag ccctggaact gccagcggcg gtcgagccct gtgtgaggga  180
ggggtgtgtg gcccagg                                                 197
```

<210> SEQ ID NO 11
<211> LENGTH: 151
<212> TYPE: DNA
<213> ORGANISM: Artificial Sequence
<220> FEATURE:
<223> OTHER INFORMATION: Synthetic

<400> SEQUENCE: 11
ttttaaagaa atatttatat tgtatttata taatgtataa atggttttta taccaataaa      60
tggcatttta aaaaattcag caactttgag tgtgtcacgc tcccgggctc gataactata     120
acggtcctaa ggtagcgact cgagataact t                                    151

<210> SEQ ID NO 12
<211> LENGTH: 128
<212> TYPE: DNA
<213> ORGANISM: Artificial Sequence
<220> FEATURE:
<223> OTHER INFORMATION: Synthetic

<400> SEQUENCE: 12
tatacgaagt tatcctaggt tggagctcct aagttacatc caaacatcct cccccaaatc      60
aataattaag cacttttat gacatgtaaa gttaaataag aagtgaaagc tgcagatggt      120
gagtgaga                                                              128

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
gccctagcat gcagaatgc                                                   19

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
aagaggtccc acatcctttg c                                                21

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
cccacatcca tcccaatcct gtgag                                            25

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
gagcttgccc ccagaaagg                                                   19

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cggccacatc tctggaagac                                               20

<210> SEQ ID NO 18
<211> LENGTH: 28
<212> TYPE: DNA
<213> ORGANISM: Artificial Sequence
<220> FEATURE:
<223> OTHER INFORMATION: Synthetic

<400> SEQUENCE: 18
catgcactgc cccaagtctg gtttcagt                                      28

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
ggagagggca gaggcactta c                                             21

<210> SEQ ID NO 20
<211> LENGTH: 19
<212> TYPE: DNA
<213> ORGANISM: Artificial Sequence
<220> FEATURE:
<223> OTHER INFORMATION: Synthetic

<400> SEQUENCE: 20
ggccagagcc caagaaaag                                                19

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
cccgttgact gtaatctgcc cctgg                                         25

<210> SEQ ID NO 22
<211> LENGTH: 191
<212> TYPE: DNA
<213> ORGANISM: Artificial Sequence
<220> FEATURE:
<223> OTHER INFORMATION: Synthetic

<400> SEQUENCE: 22
cgagggcgac tgctctcgct gccccagtct gccggccgcc cggccccggc tgcggagccg    60
ctctgccgcc cgccgtcccg cgtagaagga agcatgctgg ccgtcggctg cgcgctgctg   120
gctgccctgc tggccgcgcc gggagcggcg ctggccccaa ggcgctgccc tgcgcagggt   180
aagggcttcg g                                                       191

```
<210> SEQ ID NO 23
<211> LENGTH: 148
<212> TYPE: DNA
<213> ORGANISM: Artificial Sequence
<220> FEATURE:
<223> OTHER INFORMATION: Synthetic

<400> SEQUENCE: 23
caagattatt ggagtctgaa atggaatacc tgttgaggga aatctttatt ttgggagccc      60
ttgatttcaa tgcttttgat tccctatccc tgcaagaccc gggctcgata actataacgg     120
tcctaaggta gcgactcgag ataacttc                                        148

<210> SEQ ID NO 24
<211> LENGTH: 129
<212> TYPE: DNA
<213> ORGANISM: Artificial Sequence
<220> FEATURE:
<223> OTHER INFORMATION: Synthetic

<400> SEQUENCE: 24
tatacgaagt tatcctaggt tggagctcta ctccatatgc tcacttgccg ttgtttgcta      60
cgatacggtg aggcccgtgc gaagagtggc acagatcagg aggcttatgt ggtcagtcca     120
cagtatggc                                                             129
```